(12) United States Patent
Sierra et al.

(10) Patent No.: US 11,740,205 B2
(45) Date of Patent: *Aug. 29, 2023

(54) SENSORS, SYSTEMS AND METHODS FOR DETECTING ANALYTES USING SAME

(71) Applicant: MODOC TECHNOLOGIES, LLC, Los Altos Hills, CA (US)

(72) Inventors: David H. Sierra, Los Altos Hills, CA (US); Andrew Korey, Los Altos Hills, CA (US)

(73) Assignee: MODOC TECHNOLOGIES, LLC, Los Altos Hills, CA (US)

( * ) Notice: Subject to any disclaimer, the term of this patent is extended or adjusted under 35 U.S.C. 154(b) by 315 days.

This patent is subject to a terminal disclaimer.

(21) Appl. No.: 16/849,637

(22) Filed: Apr. 15, 2020

(65) Prior Publication Data

US 2020/0348264 A1 Nov. 5, 2020

Related U.S. Application Data

(63) Continuation of application No. 15/531,978, filed as application No. PCT/US2015/062753 on Nov. 25, 2015, now Pat. No. 10,656,123.

(Continued)

(51) Int. Cl.
*G01N 29/02* (2006.01)
*G01N 33/487* (2006.01)
(Continued)

(52) U.S. Cl.
CPC ....... *G01N 29/022* (2013.01); *G01N 29/2443* (2013.01); *G01N 33/48707* (2013.01);
(Continued)

(58) Field of Classification Search
CPC ............. G01N 29/022; G01N 29/2443; G01N 33/48707; G01N 33/54306;
(Continued)

(56) References Cited

U.S. PATENT DOCUMENTS 5,986,066 A * 11/1999 Barner ............. G01N 33/54353
977/714
2004/0020275 A1 5/2004 Paul et al.
(Continued)

FOREIGN PATENT DOCUMENTS

EP 1 804 059 7/2007

OTHER PUBLICATIONS

Suri et al, "Development of piezoelectric crystal based microgravimetric immunoassay for determination of insulin concentration", Journal of Biotechnology, 39, 1995, 27-34 (Year: 1995).*
(Continued)

*Primary Examiner* — Christopher L Chin
(74) *Attorney, Agent, or Firm* — Haynes and Boone LLP

(57) ABSTRACT

Sensors, as well as systems and methods of using the same are provided. Aspects of the sensors include a piezoelectric base, a plurality of surface-associated compositions that are stably associated with the piezoelectric base, and a plurality of crosslinking compositions that are configured to crosslink one or more surface-associated compositions in the presence
(Continued)

of an analyte. The sensors, systems and methods described herein find use in a variety of applications, including the detection of an analyte in a sample.

3 Claims, 23 Drawing Sheets

Related U.S. Application Data

(60) Provisional application No. 62/086,036, filed on Dec. 1, 2014.

(51) Int. Cl.
  *G01N 33/543* (2006.01)
  *G01N 29/24* (2006.01)

(52) U.S. Cl.
  CPC . *G01N 33/54306* (2013.01); *G01N 33/54373* (2013.01); *G01N 2291/0255* (2013.01); *H05K 2203/1333* (2013.01)

(58) Field of Classification Search
  CPC ..... G01N 33/54373; G01N 2291/0255; G01N 2021/1708; G01N 29/2437; G01N 2203/0051; H05K 2203/1333; H03H 3/02
  USPC .............. 73/514.34; 310/311, 340; 427/2.13; 436/524, 527, 828
  See application file for complete search history.

(56) References Cited

U.S. PATENT DOCUMENTS

| | | |
|---|---|---|
| 2004/0147038 A1 | 7/2004 | Lewis et al. |
| 2006/0024813 A1 | 2/2006 | Warthoe |
| 2006/0213271 A1* | 9/2006 | Edmonson ......... G01N 29/4481 422/68.1 |
| 2007/0204679 A1 | 9/2007 | Fitch et al. |
| 2008/0197750 A1 | 8/2008 | Katardjiev et al. |
| 2010/0291711 A1* | 11/2010 | Atashbar .............. G01N 27/127 422/69 |
| 2011/0053139 A1 | 3/2011 | Larson et al. |
| 2011/0177584 A1 | 7/2011 | Kadoya et al. |
| 2013/0109039 A1 | 2/2013 | Kristensen et al. |

OTHER PUBLICATIONS

Pribyl et al, "Development of piezoelectric immunosensors for competitive and direct determination of atrazine", Sensors and Actuators B 91, 2003, 333-341 (Year: 2003).*
PCT/US2015/062753, Extended European Search Report dated Jun. 14, 2018.
Stubbs et al., "Gas Phase Activity of Anti-FITC Antibodies Immobilized on a Surface Acoustic Wave Resonator Device," (2002) Biosensors and Bioelectronics 17(6-7):471-477.
Ye et al., "Piezoelectric Biosensors for Detection of *Salmonella typhimurium*," (1997) Journal of Food Science 62(5):1067-1071.

\* cited by examiner

| Log CFUs/mL | Mean | SD | CV (%) |
|---|---|---|---|
| 0 | 7904 | 948 | 11.9 |
| 2 | 8537 | 1588 | 18.6 |
| 3 | 9387 | 422 | 4.5 |
| 4 | 11591 | 1144 | 9.9 |
| 5 | 14593 | 2255 | 15.5 |
| 7 | 17352 | 4459 | 25.7 |
| 9 | 19055 | 2424 | 12.7 |

Delta frequency (Hz)

N = 4 each concentration

FIG. 13

| Sensor Description | Test Solution | Delta Frequency (Hz) | CV(%) |
|---|---|---|---|
| Protein A + 100 uL of 10 ug/mL polyclonal Ab solution | PBS | 1574 | 4.5 |
| Protein A + 100 uL of 10 ug/mL polyclonal Ab solution | SH ($10^5$ CFUs/mL) | 3769 | 6.5 |
| Protein A + 100 uL of 100 ug/mL polyclonal Ab solution | PBS | 3334 | 3.2 |
| Protein A + 100 uL of 100 ug/mL polyclonal Ab solution | SH ($10^5$ CFUs/mL) | 13,647 | 5.7 | n=3

FIG. 15

| n = 3 | anti ST (µg/mL) | Protein G (mg/mL) | Delta Freq. (hertz (CV%)) |
|---|---|---|---|
| | 0 | 0 | |
| | 1 | 0 | 1530 (1.2%) |
| | 10 | 0 | 1784 (5.4%) |
| | 100 | 0 | 126 (3.4%) |
| | 0 | 0.5 | 2749 (3.8%) |
| | 1 | 0.05 | 2194 (8.6%) |
| | 10 | 0.05 | 1812 (7.6%) |
| | 100 | 0.05 | 545 (2.8%) |
| | 1 | 0.5 | 1558 (4.2%) |
| | 10 | 0.5 | 2274 (4.5%) |
| | 100 | 0.5 | 4657 (6.7%) |
| | 100 | 1.0 | 4231 (6.0%) |
| | 100 | 3.0 | 18,038 (4.8%) |
| | 100 | 0.5 Protein A | 25,828 (6.3%) |
| | 10 | | 1742 (3.9%) |

FIG. 17

100 ug/mL Biotin-Protein G

| | Delta F, Hz (mean) | CV (%) | n |
|---|---|---|---|
| PBS control | 1499 | | 3 |
| StA, 1 mg/mL | 3735 | 2.1 | 3 |
| StA, 0.1 mg/mL | 3470 | 0.7 | 4 |
| | | 1.9 | 4 |

FIG. 18

10 ug/mL Biotin-Protein G

| | Delta F, Hz (mean) | CV (%) | n |
|---|---|---|---|
| PBS control | 1229 | 4.8 | 3 |
| StA, 1 mg/mL | 1506 | 5.3 | 4 |
| StA, 0.1 mg/mL | 2166 | 1.2 | 4 |

FIG. 19

| Sensor Description | Delta Frequency (Hz (CV%)) |
|---|---|
| Liquid state components | 1924 (0.82%) |
| Dry state control, 100 uL ST solution | 16,211 (4.0%) |
| Dry state mass control, 300 uL ST solution | 35,102 (2.7%) |
| Dry state control, 100 uL PBS | 2809 (9.9%) |
| Dry state mass control, 300 uL PBS | 7917 (8.6%) | n=3

FIG. 20

| CFUS/ml | | S.E. | | | | TMB | | | | S.H. | | | | | |
|---|---|---|---|---|---|---|---|---|---|---|---|---|---|---|---|
| | | 1:100 | | 1:1000 | | | | | | 5ug/ml | | 10ug/ml | | | |
| | | 1 | 2 | 3 | 4 | 5 | 6 | 7 | 8 | 9 | 10 | 11 | 12 | | |
| 10^2 | A | 0.183 / 0.118 | 0.125 / 0.06 | 0.197 / 0.132 | 0.206 / 0.141 | | 0.127 / 0.062 | | | 0.101 / 0.036 | 0.305 / 0.24 | 0.141 / 0.076 | 0.243 / 0.178 | 650 / Blank 650 | 10^2 |
| 10^3 | B | 0.191 / 0.126 | 0.161 / 0.096 | 0.315 / 0.25 | 0.236 / 0.171 | | 0.047 / -0.018 | | | 0.112 / 0.048 | 0.185 / 0.12 | 0.306 / 0.241 | 0.197 / 0.132 | 650 / Blank 650 | 10^3 |
| 10^4 | C | 0.23 / 0.165 | 0.236 / 0.171 | 0.273 / 0.208 | 0.223 / 0.159 | | 0.086 / 0.021 | | | 0.168 / 0.103 | 0.241 / 0.177 | 0.169 / 0.104 | 0.143 / 0.079 | 650 / Blank 650 | 10^4 |
| 10^5 | D | 0.148 / 0.084 | 0.201 / 0.136 | 0.259 / 0.195 | 0.254 / 0.189 | | 0.04 / -0.024 | | | 0.099 / 0.035 | 0.17 / 0.105 | 0.219 / 0.154 | 0.239 / 0.175 | 650 / Blank 650 | 10^5 |
| 10^6 | E | 0.241 / 0.176 | 0.203 / 0.138 | 0.23 / 0.165 | 0.194 / 0.129 | | 0.045 / -0.02 | | | 0.128 / 0.063 | 0.19 / 0.125 | 0.169 / 0.104 | 0.185 / 0.12 | 650 / Blank 650 | 10^6 |
| 10^7 | F | 0.294 / 0.229 | 0.385 / 0.32 | 0.218 / 0.153 | 0.378 / 0.313 | | 0.044 / -0.021 | | | 0.158 / 0.094 | 0.334 / 0.269 | 0.23 / 0.165 | 0.296 / 0.231 | 650 / Blank 650 | 10^7 |
| 10^7 (S.H.) | G | 0.267 / 0.202 | 0.213 / 0.148 | 0.132 / 0.067 | 0.23 / 0.166 | | | | | 0.283 / 0.218 | 0.353 / 0.288 | 0.192 / 0.127 | 0.188 / 0.123 | 650 / Blank 650 | 10^7 (S.E.) |
| | H | | | | | | | | | | | | | 650 / Blank 650 | |

FIG. 21

| | Delta F, Hz (mean) | CV (%) | n |
|---|---|---|---|
| PBS control, standard Prot G-Anti ST coatings | 1993 | 0.5 | 2 |
| ST pos. control, standard Prot G-Anti ST coatings | 4036 | 3.8 | 4 |
| ST pos. control on standard coatings incorporated with 1 ug activated carbon | 20665 | 5.1 | 3 |
| Activated carbon (100 uL sol'n) on standard coatings | 203 | 1.1 | 3 |
| PBS only, no coatings | 511 | 0.13 | 3 |

SENSORS, SYSTEMS AND METHODS FOR DETECTING ANALYTES USING SAME

CROSS REFERENCE TO RELATED APPLICATIONS

This application claims priority benefit of the filing date of U.S. Provisional Patent Application Ser. No. 62/086,036, filed on Dec. 1, 2014, the disclosure of which application is herein incorporated by reference in its entirety.

FIELD OF THE INVENTION

The present invention concerns sensors, systems and methods that find use in the detection of analytes.

BACKGROUND

Fast and accurate detection and quantification of target analytes, such as biological analytes, continues to be a major challenge in the field of bioanalytical chemistry. Frequently, analytical techniques require significant amounts of time for sample preparation and analysis, leading to significant delays between sample acquisition and reporting of test results. For example, current techniques for detecting micro-organisms in a sample frequently require culturing a sample for extended periods of time, often several days, in order to confirm the presence or absence of the micro-organism. Thus, there remains a need for sensors, systems and methods that can facilitate rapid and accurate analysis of target analytes.

SUMMARY

Sensors, as well as systems and methods of using the same are provided. Aspects of the sensors include a piezoelectric base, a plurality of surface-associated compositions that are stably associated with the piezoelectric base, and a plurality of crosslinking compositions that are configured to crosslink one or more surface-associated compositions in the presence of an analyte. The sensors, systems and methods described herein find use in a variety of applications, including the detection of an analyte in a sample.

Aspects of the invention include sensors that include a piezoelectric base, a plurality of surface-associated compositions that are stably associated with the piezoelectric base, and a plurality of crosslinking compositions that are configured to crosslink one or more surface-associated compositions in the presence of an analyte.

In some embodiments, the piezoelectric base includes at least one electrode. In some embodiments, a sensor includes an oscillator circuit that is electrically connected to the at least one electrode, and is configured to drive the sensor at one or more frequencies. In some embodiments, the oscillator circuit includes an automatic gain control (AGC) portion. In some embodiments, the surface-associated compositions include one or more of: protein A, protein G, protein A/G, or protein L. In some embodiments, the surface-associated compositions include one or more polyclonal antibodies. In some embodiments, the crosslinking compositions include one or more of: protein A, protein G, protein A/G, or protein L. In some embodiments, the crosslinking compositions include one or more polyclonal antibodies. In some embodiments, a sensor includes a computer-readable medium that contains a plurality of stored data. In some embodiments, the stored data includes a calibration value for the sensor. In some embodiments, the stored data includes an analyte signature. In some embodiments, the stored data includes an operating parameter for the sensor. In some embodiments, the piezoelectric base includes a quartz crystal. In some embodiments, the quartz crystal is an AT-cut quartz crystal. In some embodiments, the piezoelectric base has a surface texture. In some embodiments, the at least one electrode has an interdigitated structure. In some embodiments, a plurality of the surface-associated compositions and/or crosslinking compositions includes a detectable label.

Aspects of the invention include systems for detecting the presence of an analyte in a sample, the system including a sensor that includes a piezoelectric base, a plurality of surface-associated compositions that are stably associated with the piezoelectric base, a plurality of crosslinking compositions that are configured to crosslink one or more surface-associated compositions in the presence of the analyte, and at least one electrode, as well as an oscillator circuit that is electrically connected to the at least one electrode and is configured to drive the sensor at one or more frequencies, wherein the oscillator circuit includes an automatic gain control (AGC) portion, a detection unit configured to receive a plurality of data from the oscillator circuit, and a processor configured to analyze the data received from the oscillator circuit and to detect the presence of the analyte in the sample.

In some embodiments, the sensor, the oscillator circuit, the detection unit, and the processor are formed into a single device. In some embodiments, the system includes a graphical user interface. In some embodiments, the device is a hand-held device. In some embodiments, the sensor and the detection unit are separate elements, and the sensor is adapted to connect to the detection unit. In some embodiments, the system includes a plurality of sensors and a plurality of oscillator circuits that are configured to drive each of the sensors at one or more frequencies. In some embodiments, the detection unit includes a frequency spectrum analyzer. In some embodiments, the detection unit is configured to transmit an analysis result obtained from the sample to a separate location. In some embodiments, the detection unit is configured to wirelessly transmit the analysis result to the separate location. In some embodiments, the analysis result includes a geographical location from which the sample was collected. In some embodiments, the surface-associated compositions include one or more of: protein A, protein G, protein A/G, or protein L. In some embodiments, the surface-associated compositions include one or more polyclonal antibodies. In some embodiments, the crosslinking compositions include one or more of: protein A, protein G, protein A/G, or protein L. In some embodiments, the crosslinking compositions include one or more polyclonal antibodies. In some embodiments, a system includes a computer-readable medium that contains a plurality of stored data. In some embodiments, the computer-readable medium is located in the sensor. In some embodiments, the computer-readable medium is located in the detection unit. In some embodiments, the stored data includes a calibration value for the sensor. In some embodiments, the stored data includes an analyte signature. In some embodiments, the stored data includes an operating parameter for the sensor. In some embodiments, the piezoelectric base of the sensor includes a quartz crystal. In some embodiments, the quartz crystal is an AT-cut quartz crystal. In some embodiments, the piezoelectric base of the sensor has a surface texture. In some embodiments, the at least one electrode has an interdigitated structure. In some embodiments, a plurality of the surface-associated compositions and/or crosslinking compositions includes a detectable label.

In some embodiments, a system includes a detection device that is configured to detect the detectable label. In some embodiments, the detection device is a spectrophotometer, a fluoroscope, or an ellipsometer.

Aspects of the invention include methods for detecting the presence of an analyte in a sample, the methods involving contacting a sensor with the sample, wherein the sensor includes a piezoelectric base, a plurality of surface-associated compositions that are stably associated with the piezoelectric base, a plurality of crosslinking compositions that are configured to crosslink one or more surface-associated compositions in the presence of the analyte, and at least one electrode, applying a current to an oscillator circuit that is electrically connected to the at least one electrode and is configured to drive the sensor at one or more frequencies, wherein the oscillator circuit includes an automatic gain control (AGC) portion, measuring one or more parameters of the sensor and/or oscillator circuit as a function of time, and analyzing the one or more parameters of the sensor and/or oscillator circuit to detect the presence of the analyte in the sample.

In some embodiments, the methods involve detecting whether the analyte is present in the sample at a concentration that is above a threshold concentration. In some embodiments, the methods involve contacting the sample with an activated carbon composition before contacting the sample with the sensor. In some embodiments, the activated carbon composition includes a carbon nanotube. In some embodiments, the methods involve driving the sensor at a plurality of frequencies, and measuring one or more parameters of the sensor and/or oscillator circuit as a function of time at each frequency. In some embodiments, measuring the one or more parameters of the sensor involves measuring a frequency, an amplitude, and/or a frequency bandwidth of a waveform that is generated in the sensor. In some embodiments, measuring the one or more parameters of the oscillator circuit involves measuring a voltage, a resistance, an admittance, an impedance, or a conductance value of the automatic gain control (AGC) portion of the oscillator circuit. In some embodiments, analyzing the one or more parameters of the sensor and/or oscillator circuit involves comparing the one or more parameters to a calibration value. In some embodiments, analyzing the one or more parameters of the sensor and/or oscillator circuit involves comparing the one or more parameters to an analyte signature. In some embodiments, the one or more parameters of the sensor and/or oscillator circuit are measured and analyzed to detect the presence of the analyte in the sample in less than 10 seconds after the sensor is contacted with the sample. In some embodiments, a plurality of the surface-associated compositions and/or crosslinking compositions includes a detectable label, and the method involves detecting the detectable label using a detection device.

Aspects of the invention include methods of making a sensor, the methods involving depositing a plurality of surface-associated compositions on a piezoelectric base, wherein the plurality of surface-associated compositions are adapted to stably associate with the piezoelectric base, and depositing a plurality of crosslinking compositions on top of the surface-associated compositions, wherein the crosslinking compositions are configured to crosslink one or more of the surface-associated compositions in the presence of an analyte.

In some embodiments, the surface-associated compositions include one or more of: protein A, protein G, protein A/G, or protein L. In some embodiments, the surface-associated compositions include one or more polyclonal antibodies. In some embodiments, the crosslinking compositions include one or more of: protein A, protein G, protein A/G, or protein L. In some embodiments, the crosslinking compositions include one or more polyclonal antibodies. In some embodiments, depositing the plurality of surface-associated compositions on the piezoelectric base involves contacting the piezoelectric base with a solution that includes the plurality of surface-associated compositions. In some embodiments, the solution that includes the plurality of surface-associated compositions has a concentration of surface-associated compositions ranging from 0.1 µg/mL to 10 mg/mL. In some embodiments, depositing the plurality of crosslinking compositions on top of the surface-associated compositions involves contacting the plurality of surface-associated compositions with a solution that includes the plurality of crosslinking compositions. In some embodiments, the solution that includes the plurality of crosslinking compositions has a concentration of crosslinking molecules ranging from 0.1 µg/mL to 10 mg/mL. In some embodiments, the plurality of surface-associated compositions and/or the plurality of crosslinking compositions includes a detectable label.

Aspects of the invention include methods of making a sensor, the methods involving depositing a plurality of first molecules on a surface of a piezoelectric base, wherein the plurality of first molecules are configured to stably associate with the piezoelectric base, and are also configured to stably associate with one or more second molecules, depositing a plurality of the second molecules on top of the plurality of first molecules, and allowing the first and second molecules to self-assemble into a plurality of surface-associated compositions and a plurality of crosslinking compositions, wherein each of the surface-associated compositions and the crosslinking compositions each contain at least one first molecule and an least one second molecule. In some embodiments, first molecule is protein A, protein G, protein A/G, or protein L, and the second molecule is a polyclonal antibody.

Aspects of the invention include kits that include two or more sensors packaged in a sterile package, wherein each sensor includes a piezoelectric base, a plurality of surface-associated compositions that are stably associated with the piezoelectric base, and a plurality of crosslinking compositions that are configured to crosslink one or more surface-associated compositions in the presence of an analyte.

In some embodiments, the first sensor is adapted to detect a first analyte, and the second sensor is adapted to detect a second analyte that is different from the first analyte. In some embodiments, a plurality of the surface-associated compositions and/or crosslinking compositions on the two or more sensors includes a detectable label, and the kit includes a reagent that is configured to facilitate detection of the detectable label. In some embodiments, a kit includes an activated carbon composition. In some embodiments, the activated carbon composition includes a carbon nanotube. In some embodiments, a kit includes one or more sample collection devices.

BRIEF DESCRIPTION OF THE DRAWINGS

FIG. 13 is a table showing delta frequency response and CV % values for different sensors and different test solutions.

FIG. 15 is a table showing the delta frequency mean and CV % values for solutions having the indicated combination of components.

FIG. 17 is a table showing delta frequency mean and CV % values for sensors that were made using a 100 ug/mL biotin-protein G solution.

FIG. 18 is a table showing delta frequency mean and CV % values for sensors that were made using a 10 ug/mL biotin-protein G solution.

FIG. 19 is a table showing delta frequency mean and CV % values for liquid state and dry sensors tested with *Salmonella typhimuriam* test solutions, or PBS.

FIG. 20 is a table showing ELISA results for two different *Salmonella serovars*.

FIG. 21 is a table showing delta frequency mean and CV % values for sensors and test solutions with and without activated carbon.

DETAILED DESCRIPTION

Figure 1:
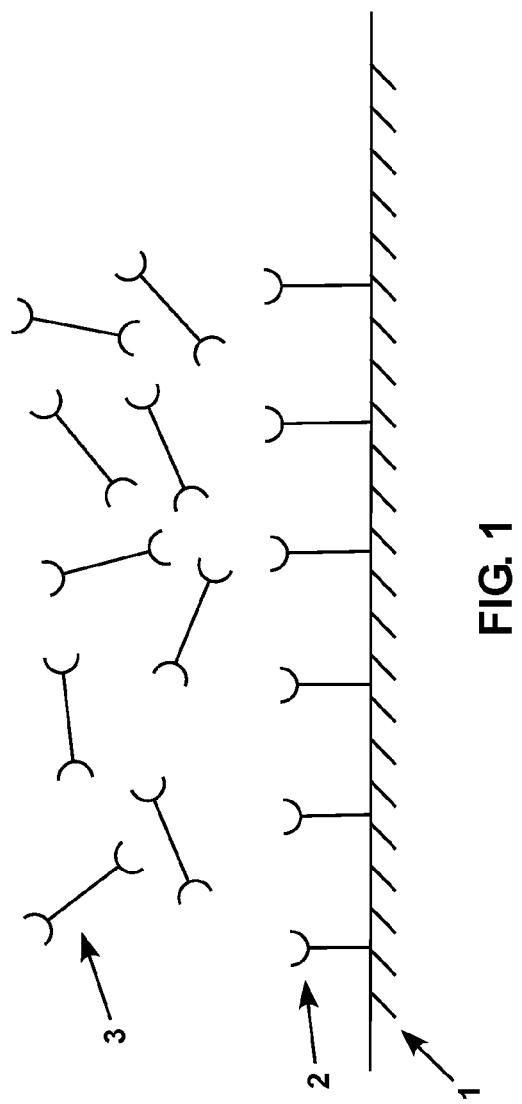
FIG. 1 is a diagram showing a schematic representation of a subject sensor with a plurality of surface-associated compositions and crosslinking compositions thereon.

Sensors, as well as systems and methods of using the same are provided. Aspects of the sensors include a piezoelectric base, a plurality of surface-associated compositions that are stably associated with the piezoelectric base, and a plurality of crosslinking compositions that are configured to crosslink one or more surface-associated compositions in the presence of an analyte. The sensors, systems and methods described herein find use in a variety of applications, including the detection of an analyte in a sample.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing various aspects of embodiments of the invention in greater detail, aspects of the systems and devices of various embodiments are reviewed first in greater detail, followed by a discussion of methods and kits according to certain embodiments of the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Sensors

Aspects of the invention include sensors that are configured to detect an analyte in a sample. The subject sensors include a piezoelectric base, a plurality of surface-associated compositions that are stably associated with the piezoelectric base, and a plurality of crosslinking compositions that are configured to crosslink one or more surface-associated compositions in the presence of an analyte. Each of these elements is described in detail below.

Surface-Associated Compositions

Surface-associated compositions in accordance with embodiments of the invention are configured to stably associate with a piezoelectric base while maintaining the ability to specifically bind to an analyte. By "stable association" or "stably associate" is meant that a first molecule or a portion thereof (e.g., a moiety) is bound to or otherwise associated with a second molecule, or with a structure (e.g., a surface of a substrate) under standard conditions. In certain instances, a stable association may create one or more bonds between the first and second molecules, or between the first molecule and the structure, which bonds may include, e.g., covalent or non-covalent interactions, such as, but not limited to, ionic bonds, hydrophobic interactions, hydrophilic interactions, hydrogen bonds, van der Waals forces, (e.g., London dispersion forces), dipole-dipole interactions, and the like. In some embodiments, the affinity between a first and a second molecule, or between a first molecule and a structure, is characterized by a $K_D$ (dissociation constant) ranging from $10^{-4}$ M to $10^{-15}$ M, such as $10^{-5}$, $10^{-6}$, $10^{-7}$, $10^{-8}$, $10^{-9}$, $10^{10}$, $10^{-11}$, $10^{-12}$, $10^{-13}$, or $10^{-14}$ M. The term "affinity" as used herein refers to the strength of the interaction between a first and a second molecule, or between a first molecule and a surface, wherein increased binding affinity is characterized by a lower $K_D$ value.

In some embodiments, a surface-associated composition may be composed of a single molecule that is configured to stably associate with the piezoelectric base and to specifically bind to an analyte. In some embodiments, a surface-associated composition may include a plurality of different molecules, such as 2, 3, 4, 5, 6, 7, 8, 9 or 10 or more molecules. In such embodiments, the molecules that make up the surface-associated composition are configured to associate with one another to form the composition. For example, in some embodiments, a surface-associated composition may include a first molecule that is configured to stably associate with a piezoelectric base, and a second molecule that is configured to specifically bind to an analyte. In such embodiments, the first molecule is configured to stably associate with the piezoelectric base, and is also configured to stably associate with the second molecule to form a surface-associated composition.

Surface-associated compositions in accordance with embodiments of the invention include one or more surface binding domains that are configured to stably associate with a substrate (e.g., a piezoelectric base). In some embodiments, a surface binding domain may include: a cyanogen bromide linkage (e.g., a cyanate ester linkage); an NHS ester linkage; an aldehyde linkage; an azlactone ring linkage; a carbonyl diimidazole linkage; a sulfhydryl (thiol) linkage; a maleimide linkage; an iodoacetyl linkage; a pyridyl disulfide linkage; a hydrazide linkage; or a carbodiimide linkage.

In some embodiments, a surface binding domain is configured to adsorb to a surface (e.g., a surface of a piezoelectric base, or a surface of an electrode) to stably associate with the surface. In some embodiments, the material properties of the surface may be configured to promote stable association with the surface binding domain. For example, in some embodiments, the surface material, surface energy, texture, and/or charge distribution on the surface may be selected and/or modulated to promote stable association with a surface binding domain.

In some embodiments, a surface-associated composition may include one or more polypeptides that have a surface binding domain. In such embodiments, the surface binding domain of the polypeptide is configured to stably associate with the piezoelectric base of the sensor. Examples of polypeptides that include a surface binding domain include, but are not limited to: protein A, protein G, protein A/G and protein L.

In some embodiments, a surface-associated composition includes two or more molecules that are configured to stably associate with one another to form the surface-associated composition. In such embodiments, at least one of the molecules includes at least one binding domain that is configured to form a stable association between the two or more molecules. For example, in some embodiments, a surface-associated composition may include a first molecule that includes a surface binding domain configured to form a stable association with the piezoelectric base, and also includes a binding domain that is configured to stably associate with at least one other molecule (e.g., an analyte binding molecule) to form a surface-associated composition.

In some embodiments, a surface-associated composition may include a first molecule that includes a plurality of surface binding domains that are configured to form a stable association with the piezoelectric base, and also includes a plurality of binding domains that are configured to stably associate with a plurality of other molecules to form a surface-associated composition. For example, in some embodiments, a surface-associated composition may include a first molecule that has 2, 3, 4, 5, 6, 7, 8, 9 or 10 or more surface binding domains that are configured to form a stable association with the piezoelectric base, and also has 2, 3, 4, 5, 6, 7, 8, 9 or 10 or more binding domains that are each configured to stably associate with another molecule (e.g., an analyte-binding molecule) to a form a surface-associated composition.

In some embodiments, a surface-associated composition includes a protein molecule that has a surface binding domain and also includes one or more immunoglobulin binding domains that are configured to form a stable association with an immunoglobulin molecule (e.g., an antibody). Examples of protein molecules that include at least one immunoglobulin binding domain include, but are not limited to: protein A, protein G, protein A/G and protein L.

Surface-associated compositions in accordance with embodiments of the invention include one or more analyte binding domains that are configured to specifically bind to an analyte. Specific binding between an analyte and an analyte binding domain results in the formation of a stable association between the analyte and the analyte binding domain. Depending on the nature of the analyte, an analyte binding domain may include, for example, a member of a receptor/ligand pair; a ligand-binding portion of a receptor; a member of an antibody/antigen pair; an antigen-binding fragment of an antibody; a hapten; a member of a lectin/carbohydrate pair; a member of an enzyme-substrate pair; biotin/avidin; biotin/streptavidin; digoxin/antidigoxin; a member of a DNA or RNA aptamer binding pair; a member of a peptide aptamer binding pair; a member of a metal/metal-binding peptide pair; a chelating agent; and the like.

In some embodiments, an analyte binding domain of a surface-associated composition includes an antigen. The antigen may specifically bind to an analyte in a sample, such as an antibody of interest in the sample, or a fragment thereof. In some embodiments, an analyte binding domain includes an antibody, or an antibody fragment. The antibody may specifically bind to an analyte of interest in a sample, such as an antigen of interest in the sample.

In some embodiments, a sensor includes a plurality of surface-associated compositions whose analyte binding domains recognize different binding regions of an analyte. As such, in certain embodiments, two or more different analyte binding domains are each configured to bind to different portions of the same analyte (e.g., different epitopes on the same antigen).

In some embodiments, an analyte binding domain of a surface-associated composition includes an antibody. Antibodies in accordance with embodiments of the invention may be monoclonal or polyclonal, and may be any suitable class (isotype), including IgA, IgD, IgE, IgG or IgM. Antibodies in accordance with embodiments of the invention may also be any suitable subclass, including but not limited to IgG1, IgG2, IgG3 or IgG4. Antibodies may be produced by any suitable means, including but not limited to, inoculation of a suitable mammal with an antigen, followed by recovery and purification of the antibody, or through the use of recombinant antibody production technology. Antibodies may also be obtained from commercial suppliers and used in the subject sensors and systems. Antibodies in accordance with embodiments of the invention may have any suitable binding affinity for an analyte (e.g., an antigen), having a $K_D$ value ranging from $10^{-4}$ to $10^{-15}$, such as $10^{-5}$, $10^{-6}$, $10^{-7}$, $10^{-8}$, $10^{-9}$, $10^{-10}$, $10^{-11}$, $10^{-12}$, $10^{13}$, or $10^{-14}$.

Antibody fragments and conjugates may also be used as analyte binding domains in the subject surface-associated compositions, and as such, references made herein to the term "antibody" or "antibodies" are to be understood as including full length antibodies as well as any fragments and/or conjugates thereof. Antibody fragments, for example, include but are not limited to Fv, F(ab), F(ab'), F(ab')2, and single-chain antibodies having one full-length heavy chain and one full-length light chain. In some embodiments, an antibody may be a hybrid antibody that includes one or more portions of a first antibody that are functionally attached or connected to one or more portions of a second antibody. Antibody conjugates include, for example, antibodies that are bound to one or more detectable label moieties and/or reporter compounds, such as, e.g., enzymes, enzyme substrates, radioactive or colorimetric labels, and the like.

In some embodiments, a surface-associated composition may include one or more detectable label moieties and/or reporter compounds, such as, e.g., enzymes, enzyme substrates, radioactive or colorimetric labels, and the like, in order to facilitate detection of the surface-associated composition.

Crosslinking Compositions

Crosslinking compositions in accordance with embodiments of the invention are present on the sensor and are configured to crosslink one another, as well as one or more surface-associated compositions, in the presence of an analyte. Crosslinking compositions in accordance with embodiments of the invention include at least two analyte binding domains that are configured to specifically bind to an analyte. In some embodiments, a crosslinking composition may include 3, 4, 5, 6, 7, 8, 9 or 10 or more analyte binding domains.

Specific binding between an analyte and an analyte binding domain results in the formation of a stable association between the analyte and the analyte binding domain. Depending on the nature of the analyte, an analyte binding domain may include, for example, a member of a receptor/ligand pair; a ligand-binding portion of a receptor; a member of an antibody/antigen pair; an antigen-binding fragment of an antibody; a hapten; a member of a lectin/carbohydrate pair; a member of an enzyme-substrate pair; biotin/avidin; biotinlstreptavidin; digoxin/antidigoxin; a member of a DNA or RNA aptamer binding pair; a member of a peptide aptamer binding pair; a member of a metal/metal-binding peptide pair; a chelating agent; and the like.

In some embodiments, an analyte binding domain of a crosslinking composition includes an antigen. The antigen may specifically bind to an analyte in a sample, such as an antibody of interest in the sample, or a fragment thereof. In some embodiments, an analyte binding domain includes an antibody, or an antibody fragment. The antibody may specifically bind to an analyte of interest in a sample, such as an antigen of interest in the sample.

In some embodiments, a sensor includes a plurality of crosslinking compositions whose analyte binding domains recognize different binding regions of an analyte. As such, in certain embodiments, two or more different analyte binding domains are each configured to bind to different portions of the same analyte (e.g., different epitopes on the same antigen).

In some embodiments, an analyte binding domain of a crosslinking composition includes an antibody. Antibodies in accordance with embodiments of the invention may be monoclonal or polyclonal, and may be any suitable class (isotype), including IgA, IgD, IgE, IgG or IgM. Antibodies in accordance with embodiments of the invention may also be any suitable subclass, including but not limited to IgG1, IgG2, IgG3 or IgG4. Antibodies may be produced by any suitable means, including but not limited to, inoculation of a suitable mammal with an antigen, followed by recovery and purification of the antibody, or through the use of recombinant antibody production technology. Antibodies may also be obtained from commercial suppliers and used in the subject sensors and systems. Antibodies in accordance with embodiments of the invention may have any suitable binding affinity for an analyte (e.g., and antigen), having a $K_D$ value ranging from $10^{-4}$ to $10^{-15}$, such as $10^{-5}$, $10^{-6}$, $10^{-7}$, $10^{-8}$, $10^{-9}$, $10^{-19}$, $10^{-11}$, $10^{-12}$, $10^{-13}$, or $10^{-14}$.

Antibody fragments and conjugates may also be used as analyte binding domains in the subject crosslinking compositions. Antibody fragments, for example, include but are not limited to Fv, F(ab), F(ab'), F(ab')2, and single-chain antibodies having one full-length heavy chain and one full-length light chain. In some embodiments, an antibody may be a hybrid antibody that includes one or more portions of a first antibody that are functionally attached or connected to one or more portions of a second antibody. Antibody conjugates include, for example, antibodies that are bound to one or more detectable label moieties and/or reporter compounds, such as, e.g., enzymes, enzyme substrates, radioactive or colorimetric labels, and the like.

In some embodiments, a crosslinking composition may be composed of a single molecule that has two or more analyte binding domains that are configured to specifically bind to an analyte. In some embodiments, a crosslinking composition may include a plurality of different molecules, such as 2, 3, 4, 5, 6, 7, 8, 9 or 10 or more molecules. In such embodiments, the molecules that make up the crosslinking composition are configured to stably associate with one another to form the crosslinking composition. For example, in some embodiments, a crosslinking composition may include a first molecule with a first analyte binding domain, and a second molecule with a second analyte binding domain. In such embodiments, the first molecule is configured to stably associate with the second molecule to form a crosslinking composition.

In some embodiments, a crosslinking composition includes a polypeptide that has one or more immunoglobulin binding domains that are configured to form a stable association with an immunoglobulin molecule (e.g., an antibody). Examples of polypeptides that include at least one immunoglobulin binding domain include, but are not limited to: protein A, protein G, protein A/G and protein L. In some embodiments, a crosslinking composition may include a polypeptide molecule with two immunoglobulin binding domains, wherein one immunoglobulin molecule (e.g., an antibody) is stably associated with each of the immunoglobulin binding domains.

In some embodiments, a crosslinking composition may include one or more detectable label moieties and/or reporter compounds, such as, e.g., enzymes, enzyme substrates, radioactive or colorimetric labels, and the like, in order to facilitate detection of the surface-associated composition.

Analytes

The subject sensors may be configured to detect any target analyte of interest. Analytes of interest include, but are not limited to, organic and inorganic molecules, environmental pollutants (e.g., heavy metals, pesticides), chemical compounds, therapeutic drugs, drugs of abuse, biomolecules (e.g., hormones, cytokines, proteins, lipids, carbohydrates, nucleic acids), cells, parasites, viruses, bacteria, and fungi (e.g., spores). Analytes of interest also include, but are not limited to, food borne and other pathogens, such as microbes, e.g., parasites, bacteria, viruses, fungi, or any toxins produced thereby. In reference to an analyte that is a microbe, (including a cell, parasite, virus, bacterium or fungus), analytes of interest include any portion of a microbe (e.g., a molecule or portion thereof that is a part of the microbe). Non-microbe analytes of interest include, but are not limited to, molecules or portions thereof that may be produced by a microbe (e.g., a toxin or other molecule that is produced by a microbe).

Bacteria that may be detected using the subject sensors include, but are not limited to: gram positive bacteria, e.g., *Actinomyces, Bacillus, Clostridium, Corynebacterium, Enterococcus, Gardnerella, Lactobacillus, Listeria, Mycobacterium, Mycoplasma, Nocardia, Propionibacterium, Staphylococcus* (such as *S. aureus, S. epidermidis*), *Streptococcus* (such as α-hemolytic *Streptococcus* (e.g., *pneumoniae*, Viridens), β-hemolytic *Streptococcus* (e.g., *pyogenes, agalactiae*) and γ-hemolytic *Streptococcus* (e.g., *enterococcus*)), and *Streptomyces*; and gram negative bacteria, e.g., *Acetobacter, Borrelia, Bortadella, Burkholderia, Campylobacter, Chlamydia, Enterobacter*, Eschrichia (such as *E. Coli* and *Salmonella*), *Fusobacterium, Helicobacter, Haemophilus, Klebsiella, Legionella, Leptospiria, Neisseria, Nitrobacter, Proteus, Pseudomonas, Rickettsia, Salmonella, Serratia, Shigella, Thiobacter, Treponema, Vibrio,* and *Yersinia*.

Viruses that may be detected using the subject sensors include, but are not limited to: double stranded DNA viruses, e.g., Caudoviruses, Herpesviruses, Ligamenviruses, Adenoviruses, Polyomaviruses, and Poxviruses; single stranded DNA viruses, e.g., Anelloviruses, Circoviruses, Nanoviruses and Parvoviruses; double stranded RNA viruses, e.g., Alternaviruses, Chrysoviruses, and Reoviruses; positive-sense (+) single stranded RNA viruses, e.g., Caliciviruses (such as Norovirus), Nidoviruses, Picornaviruses, Tymoviruses, Flaviviruses, Togaviruses, and Hepeviruses; negative sense (−) single stranded RNA viruses, e.g., Mononegaviruses (such as Filoviruses, including Ebola virus and Marburg virus), Bunyaviruses (such as Hantavirus), Orthomyxoviruses (such as Influenza virus) and Deltaviruses; single stranded RNA reverse transcriptasc (RT) viruses, e.g., Metaviruses, Pseudoviruses and Retroviruses (such as Human Immunodeficiency Virus (HIV)); and double stranded DNA reverse transcriptase (RT) viruses, e.g., Hepadnaviruses (such as Hepatitis B virus) and Caulimoviruses.

Fungi that may be detected using the subject sensors include: Microsporidia (such as *Brachiola, Encephalitozoon, Entercytozoon, Microsporidium, Nosema, Pleistophora, Trachipleistophora,* and *Vittaforma*); Chytridiomycota; Blastocladiomycota; Neocallimastigomycota; Glomeromycota; Ascomycota (such as *Aspergillus, Candida, Coccidioidcs, Histoplasma*); and Basidiomycota (such as *Cryptococcus*).

Parasites that may be detected using the subject sensors include, but are not limited to: protozoan organisms (such as Giardia, Malaria, *Toxoplasma gondii* and Trypanosomes); and helminthes organisms (such as tapeworms, roundworms, and flukes).

Examples of non-microbe analytes of interest include, but are not limited to: Botulinum neurotoxins; Tetanus toxin; Staphylococcal toxins; Alpha toxin; Anthrax toxin; Diptheria toxin; Exotoxin; Pertussis toxin; Shiga toxin and Shiga-like toxin.

Piezoelectric Base

The subject sensors include a piezoelectric base, or substrate. A piezoelectric base in accordance with embodiments of the invention includes a material that produces an electrical charge when a mechanical stress is imposed on the material, and produces a mechanical stress when an electrical charge is imposed on the material. The subject sensors function by applying an oscillating electric field to the piezoelectric base to create a mechanical wave therein. The wave propagates through the piezoelectric base and is converted into an electrical signal for measurement. The resonant frequency of the piezoelectric base can be measured, and changes in the resonant frequency resulting from changes in the mechanical properties of the sensor (e.g., from the formation of crosslinks between the surface-associated compositions and the crosslinking compositions in the presence of an analyte) can be utilized to qualitatively and/or quantitatively determine the amount of an analyte that is bound to the molecules on the sensor.

A piezoelectric base in accordance with embodiments of the invention may have any suitable size and shape. In some embodiments, a piezoelectric base may be circular, oval, square, rectangular, or hexagonal in shape. In some embodiments, the piezoelectric base may include a textured surface. Piezoelectric base components are commercially available in various forms, such as wafers or discs of suitable sizes and shapes. Commercial suppliers of piezoelectric components and materials include, for example International Crystal Manufacturing Co. Inc. (ICM, Inc., Oklahoma City, Okla.). In some embodiments, a piezoelectric base may have a length dimension that ranges from 2 to 50 mm, such as 5, 10, 15, 20, 25, 30, 35, 40 or 45 mm. In some embodiments, a piezoelectric base may have a width dimension that ranges from 2 to 50 mm, such as 5, 10, 15, 20, 25, 30, 35, 40 or 45 mm. In some embodiments, a piezoelectric base may have a diameter that ranges from 2 to 50 mm, such as 5, 10, 15, 20, 25, 30, 35, 40 or 45 mm.

Sensors in accordance with embodiments of the invention may have a piezoelectric base with a thickness that varies, where in some instances the thickness ranges from 10 µm to 5 mm, such as 50, 100, 200, 300, 400, 500, 600, 700, 800, or 900 µm or more, such as 1, 2, 3 or 4 mm. In some embodiments, the thickness of the piezoelectric base is uniform, e.g., is the same at each position on the piezoelectric base, while in some embodiments, the thickness of the piezoelectric base is variable, e.g., is different at different positions on the piezoelectric base.

Piezoelectric base materials in accordance with embodiments of the invention include, but are not limited to, quartz ($SiO_2$), berlinite ($AlPO_4$), gallium orthophosphate ($GaPO_4$), tourmaline, barium titanate ($BaTiO_3$), lead zirconate titanate (PZT), zinc oxide (ZnO), aluminum nitride (AiN), polyvinylidene fluoride (PVDF), lithium tantalite ($LiTaO_3$), lanthanum gallium silicate and potassium sodium tartrate ($KNaC_4H_4O_6 \cdot 4H_2O$). In some embodiments, the piezoelectric base is an AT cut quartz crystal. In some embodiments, the piezoelectric base is an SC cut quartz crystal.

In some embodiments, a piezoelectric base may be disposed on or in a non-piezoelectric material. Suitable non-piezoelectric materials include, but are not limited to: polymeric materials (e.g., plastics); metals; glasses; ceramics; or any combination thereof. In some embodiments, a sensor may include a non-piezoelectric material that structurally supports the piezoelectric base. In such embodiments, a piezoelectric base may be mounted on a non-piezoelectric material. For example, in some embodiments, a piezoelectric base may be mounted on a surface of a non-piezoelectric material. In some embodiments, a sensor may include a non-piezoelectric material having a depression or concavity therein, and the piezoelectric base may be placed in the depression or concavity.

Electrodes

Electrodes in accordance with embodiments of the invention may have any suitable geometry and dimensions, and may be located on the piezoelectric base to suitably control the application of electrical charge to, and the detection of electrical charge in, the piezoelectric base material. For example, in some embodiments, the dimensions of an electrode may range from 1 µm to 50 mm, such as 10, 20, 30, 40, 50, 60, 70, 80 or 90 µm, or such as 0.1, 1, 10, 20, 30 or 40 mm. The geometry and dimensions of an electrode may be varied in order to conform to the shape of the piezoelectric base material. For example, in some embodiments, an electrode may include a portion having a rectangular shape, and/or an arced, circular, or semi-circular shape.

In some embodiments, an electrode may be formed into an interdigitated structure, meaning that the electrode includes a first and second plurality of comb-like projections that are configured to interlock with one another to form a zipper-like pattern. An electrode with an interdigitated structure can be configured to convert an electrical signal into an acoustic wave that propagates through the pieozoelectric base, and vice versa. In some embodiments, a sensor may include a first electrode with an interdigitated structure that functions as an input electrode that converts an electrical signal into a mechanical wave that propagates through the piezoelectric base material, and a second electrode with an interdigitated structure that functions as an output electrode that converts a mechanical wave into an electrical signal.

Electrodes in accordance with embodiments of the invention may include any conductive material, including but not limited to, aluminum, carbon, chromium, cobalt, copper, molybdenum, nickel, palladium, platinum, silicon, silver, tin oxide, titanium, tungsten, zinc, or gold.

Electrodes in accordance with embodiments of the invention are configured to induce mechanical oscillations in the piezoelectric material when an appropriate current or voltage is applied to the electrode. In response to the applied current or voltage, the piezoelectric base is configured to vibrate at a resonant frequency. In some embodiments, the resonant frequency of the piezoelectric base ranges from 0.1-100 Hz, such as 25-75 Hz. In some embodiments, the resonant frequency of the piezoelectric base ranges from 1-100 kHz, such as 25-75 kHz. In some embodiments, the resonant frequency of the piezoelectric base ranges from 1-30 MHz, such as 10-15 MHz.

The application of a suitable electrical signal (e.g., a current or voltage) to an electrode creates a standing shear wave in the piezoelectric material, and the characteristics of the standing shear wave can be detected and measured using standard electrical circuitry and data recording devices. The frequency of oscillation of the sensor is partially dependent on the thickness of the piezoelectric base material, and changes in the thickness of the base material or its mechanical properties (e.g., the dynamic modulus of the sensor) correlate directly to one or more changes in the oscillation frequency, and/or the parameters of an oscillator circuit that is used to drive the sensor at a resonant frequency. For example, the binding of an analyte to the surface-associated compositions and crosslinking compositions results in the formation of crosslinks between the compositions on the sensor, which changes the dynamic modulus of the sensor and modulates the oscillation frequency of the sensor. Any changes in the resonant frequency of the sensor (e.g., changes in the frequency, the amplitude and/or the frequency bandwidth of the resonant frequency), and/or the parameters of the oscillator circuit that is used to drive the sensor at a resonant frequency, are measured using standard techniques, and the data is used to determine the amount of the analyte bound to the sensor. Various characteristics of the frequency change can be quantified and correlated precisely to the mass change of the piezoelectric base using Sauerbrey's equation ($\Delta m = -C \cdot \Delta f$, where $\Delta m$ is the change in mass, $\Delta f$ is the change in frequency, and $-C$ is a constant that is based on the resonant frequency, the piezoelectrically active area of the piezoelectric base, the density of the piezoelectric base material, and the shear modulus of the piezoelectric base material), thereby facilitating the quantification of the amount of analyte bound to the sensor. Aspects of the resonant frequency and standing shear wave in the piezoelectric base that can be measured include, but are not limited to, the frequency, the amplitude, and the frequency bandwidth of the waveform that is generated in the piezoelectric base.

Sensors in accordance with embodiments of the invention may include a structure that is configured to retain a liquid sample in contact with the sensor. For example, in some embodiments, a sensor may include a well that includes a walled structure that is configured to hold a volume of liquid. A well in accordance with embodiments of the invention can have any suitable shape, and may have, e.g., a square, rectangular, circular, oval, or hexagonal cross-sectional shape when viewed from above. Wells in accordance with embodiments of the invention may have a depth that varies, and in some instances may range from 1, 2, 3, 4, 5, 6, 7, 8, 9 or 10 mm deep or more, such as 1, 2, 3, 4, 5, 6, 7, 8, 9, or 10 cm deep or more. Wells in accordance with embodiments of the invention may have a length, a width, or a diameter that varies, and in some instances may range from 1, 2, 3, 4, 5, 6, 7, 8, 9, or 10 cm or more.

In some embodiments, the walls of a well may be substantially perpendicular to the bottom of the well. In certain embodiments, the walls of a well may be positioned at an angle with respect to the bottom of the well, wherein the angle may range from 80 degrees to 45 degrees, such as 50 to 70 degrees. In some embodiments, the walls of a well may be straight. In some embodiments, the walls of a well may be curved or flared, such that the diameter of the well increases or decreases in the vertical direction. In some embodiments, a well may be configured to be operatively attached or coupled to a sensor in order to facilitate retaining a liquid sample in contact with the sensor.

In some embodiments, a well is configured to hold a volume of liquid ranging from 10 μL to 10 mL, such as 50, 100, 250, 500, or 750 μL or more, such as 1, 2, 3, 4, 5, 6, 7, 8, or 9 mL or more. In some embodiments, a well is configured such that the piezoelectric base of the sensor is disposed at the bottom of the well. In some embodiments, a well is configured such that the piezoelectric base is disposed on a side of the well (e.g., on an inner surface of a wall of the well).

In some embodiments, a sensor may include a depression or concavity that is configured to retain a liquid sample in contact with the sensor. A depression in accordance with embodiments of the invention can have any suitable shape, and may have, e.g., a square, rectangular, circular, oval, or hexagonal cross-sectional shape when viewed from above. A depression in accordance with embodiments of the invention may have a depth that varies, and in some instances may range from 1, 2, 3, 4, 5, 6, 7, 8, 9 or 10 mm deep or more, such as 1, 2, 3, 4, 5, 6, 7, 8, 9, or 10 cm deep or more. In some embodiments, a depression may have a length, a width, or a diameter that varies, and in some instances may range from 1, 2, 3, 4, 5, 6, 7, 8, 9, or 10 cm or more. In some embodiments, a depression is configured to hold a volume of liquid ranging from 100 to 10 mL, such as 1 to 5 mL. In some embodiments, a depression is configured such that the piezoelectric base of the sensor is disposed at the bottom of the depression. In some embodiments, a depression is configured such that the piezoelectric base is disposed on a side of the depression.

In some embodiments, a sensor may include an extended portion (having a distal end and a proximal end) that is configured to allow the sensor to be dipped into or immersed in a liquid sample so that the sample can contact the sensor. For example, in some embodiments, a sensor may include an extended portion having a length that may range from 5 to 500 cm, such as 25 to 250 cm and a width that may range from 1 to 10 cm, such as 2 to 5 cm. In some embodiments, the extended portion may be rigid, while in some embodiments, the extended portion may be flexible and configured such that an operator can bend or shape the extended portion into a desired shape for use in contacting a sample. For example, in some embodiments, a sensor includes an extended portion that can be bent or curved by an operator to facilitate contacting the sensor with a sample. In such embodiments, the extended portion is configured such that the piezoelectric base of the sensor is disposed at the distal end of the extended portion, and is operatively connected to the other parts of the sensor. An extended portion of a sensor in accordance with embodiments of the invention can be made from any suitable material, such as plastic, metal, glass or ceramic, or any suitable combination thereof.

In some embodiments, the subject sensors include a computer-readable medium (e.g., an EPROM chip (erasable programmable read-only memory chip) that is configured to store data). The stored data may include information regarding a calibration value or parameter for the sensor, and/or an operating value or parameter for the sensor. When the sensor is coupled to a detection unit, as described further below, the data stored on the computer-readable medium of the sensor can be accessed by the detection unit and used during operation of the sensor. In some embodiments, a sensor may include a computer-readable medium that contains data relating to one or more calibration values for the sensor, or one or more calibration values for a particular manufacturing lot of sensors. In some embodiments, the computer-readable medium on the sensor may include data relating to the type and/or class of analyte that can be detected by the sensor, the type of surface-associated and/or crosslinking compositions on the sensor, the type of detectable label on the sensor, or any other useful information relating to the operation and use of the sensor with the subject systems and methods.

In some embodiments, the computer-readable medium on the sensor may include information that relates to an analyte signature. By "analyte signature" is meant a specific set of values that is generated by the sensor when a specific analyte binds to the sensor. In some embodiments, information relating to an analyte signature may be stored on the computer-readable medium of the sensor, and may be accessed by the detection unit when the sensor is coupled to the detection unit. The analyte signature information can then be used to identify and quantify the amount of an analyte in a test sample that is contacted with the sensor.

In some embodiments, a detection unit, as described further below, may include a computer-readable medium that is configured to store data. The stored data may include information regarding a calibration value or parameter for a particular sensor, and/or an operating value or parameter for a particular sensor. In some embodiments, the detection unit is configured to obtain identification information from the sensor (e.g., a particular lot number or other identifier) and to use the identification information when operating the sensor.

Sensors in accordance with embodiments of the invention may include additional components that are configured to facilitate the operative connection of the sensor to a detection unit, as described further below. In some embodiments, a sensor may include one or more electrical leads and/or electrode contacts that are configured to establish an electrical connection between the sensor and the detection unit. Electrical leads and/or electrode contacts may have any suitable geometry and/or dimensions as required to establish the necessary electrical contact between the sensor and the detection unit. In some embodiments, a sensor may include mechanical elements that are configured to connect with a detection unit to facilitate the operative connection of the sensor to the detection unit. For example, in some embodiments, a sensor may include a clip, a clasp, a snap-fit element, or any other suitable mechanical component that is configured to engage with a corresponding mechanical component on the detection unit in order to operatively couple the sensor to the detection unit. In some embodiments, a sensor and/or a detection unit may further include a release component that is configured to dis-engage the sensor from the detection unit. For example, in some embodiments, a detection unit may include a button or a lever that can be used to dis-engage a sensor from the detection unit.

Referring now to FIG. 1, an embodiment of a subject sensor that includes a plurality of surface-associated compositions and crosslinking compositions is depicted. In the depicted embodiment, the piezoelectric base 1 is shown, as well as a plurality of surface-associated compositions 2 and a plurality of crosslinking compositions 3. The depicted surface-associated compositions 2 and crosslinking compositions 3 are configured to crosslink one another in the presence of an analyte.

Methods of Making Sensors

Aspects of the invention include methods of making the subject sensors, as described above. In some embodiments, a sensor is made by contacting a piezoelectric base (or an electrode formed thereon) with a composition under conditions that facilitate the formation of a stable association between the composition and a surface of the piezoelectric base. For example, in some embodiments, a liquid that includes a plurality of surface compositions is contacted with the piezoelectric base, and the surface compositions stably associate with the piezoelectric base to form a plurality of surface-associated compositions on the piezoelectric base.

Contacting the piezoelectric base with a liquid that includes the surface compositions can be accomplished by any suitable method, including, but not limited to: immersing the piezoelectric base in the liquid; depositing the liquid on top of the piezoelectric base using, e.g., a pipette or micropipette; spraying the liquid onto the piezoelectric base, spin coating the liquid onto the piezoelectric base, etc.

The liquid that includes the plurality of surface compositions is configured to maintain the surface compositions under suitable conditions to facilitate their stable association with the piezoelectric base. As such, depending on the nature of the surface compositions, the liquid may be an aqueous or non-aqueous liquid, may contain any suitable buffering components, may have any suitable pH, and may be maintained at any suitable temperature that does not degrade the surface-associated compositions. In some embodiments, the surface-associated compositions include a polypeptide (e.g., an antibody), and the liquid is an aqueous buffer, such as water or phosphate buffered saline (PBS), having a pH that ranges from 4 to 8, such as 6 to 7, and a temperature that ranges from 5 to 20 degrees C. Any suitable amount of surface compositions may be present in the liquid. In some embodiments, the concentration of the surface compositions in the liquid ranges from 0.1 µg/mL to 10 mg/mL, such as 1 µg/mL, 100 µg/mL, 500 µg/mL, or more, such as 1 to 5 mg/mL.

After the liquid is contacted with the piezoelectric base, the liquid is allowed to evaporate, leaving a plurality of surface-associated compositions on the surface of the piezoelectric base.

Once the surface-associated compositions have stably associated with the piezoelectric base, a plurality of crosslinking compositions is deposited on top of the surface-associated compositions. For example, in some embodiments, a liquid that includes a plurality of crosslinking compositions is contacted with the sensor, and the liquid is evaporated to leave a plurality of crosslinking compositions on the sensor.

Contacting the sensor with the liquid that includes the crosslinking compositions can be accomplished by any suitable method, including, but not limited to: immersing the sensor in the liquid; depositing the liquid on top of the sensor using, e.g., a pipette or micropipette; spraying the liquid onto the sensor, spin coating the liquid onto the sensor, etc.

The liquid that includes the plurality of crosslinking compositions is configured to maintain the crosslinking compositions under suitable conditions to facilitate their deposition on the sensor. As such, depending on the nature of the crosslinking compositions, the liquid may be an aqueous or non-aqueous liquid, may contain any suitable buffering components, may have any suitable pH, and may be maintained at any suitable temperature that does not degrade the crosslinking compositions. In some embodiments, a crosslinking composition includes a polypeptide (e.g., an antibody), and the liquid is an aqueous buffer, such as water or phosphate buffered saline (PBS), having a pH that ranges from 4 to 8, such as 6 to 7, and a temperature that ranges from 5 to 20 degrees C. Any suitable amount of crosslinking compositions may be present in the liquid. In some embodiments, the concentration of the crosslinking compositions in the liquid ranges from 0.1 µg/mL to 10 mg/mL, such as 1 µg/mL, 100 µg/mL, 500 µg/mL, or more, such as 1 to 5 mg/mL.

After the liquid is contacted with the sensor, the liquid is allowed to evaporate, leaving a plurality of crosslinking compositions deposited on top of the surface-associated compositions on the sensor. The sensor is then ready for use, as provided in greater detail herein.

In some embodiments, a sensor can be made by adding activated carbon to one or more of the solutions that are deposited on the surface. For example, in some embodiments, activated carbon is combined with the liquid that includes the plurality of surface compositions. In some embodiments, activated carbon is combined with the liquid that includes the plurality of crosslinking compositions.

In some embodiments, a sensor is made by depositing a plurality of first molecules on a surface of the piezoelectric base, and then depositing a plurality of second molecules on top of the plurality of first molecules. The first and the second molecules are members of both the surface-associated compositions and the crosslinking compositions that are to be formed on the sensor. Following their deposition on the sensor, the first and second molecules self-assemble into a plurality of surface-associated compositions that are stably associated with the piezoelectric base, and a plurality of crosslinking compositions.

For example, in some embodiments, a liquid that includes a plurality of first molecules (e.g., protein G molecules) is contacted with the piezoelectric base, and the first molecules stably associate with a surface of the piezoelectric base. The liquid includes an excess amount of the first molecules, such that the entire surface of the piezoelectric base that is available for stable association becomes covered with the first molecules. The excess first molecules remain present on the sensor, but are not stably associated with a surface of the piezoelectric base.

In some embodiments, activated carbon is combined with the liquid that includes the plurality of molecules. In some embodiments, activated carbon is combined with the liquid that includes the plurality of second molecules.

After the liquid is contacted with the piezoelectric base, the liquid is allowed to evaporate, leaving a plurality of the first molecules stably associated with the surface of the piezoelectric base, and a plurality of the first molecules present on the sensor, but not stably associated with the piezoelectric base.

Next, a liquid that includes a plurality of second molecules (e.g., a plurality of polyclonal antibodies) is deposited on top of the plurality of first molecules. A portion of the second molecules stably associate with the first molecules that are already stably associated with the surface of the piezoelectric base, thereby forming a plurality of surface-associated compositions that include a first molecule (e.g., a protein G molecule) and a second molecule (e.g., a polyclonal antibody). Another portion of the second molecules stably associate with the first molecules that are not stably associated with the surface of the piezoelectric base, thereby forming a plurality of crosslinking compositions that include a first molecule (e.g., a protein G molecule) and at least one second molecule (e.g., a polyclonal antibody). The liquid that includes the plurality of second molecules is allowed to evaporate, leaving a plurality of surface-associated compositions that are stably associated with a surface of the piezoelectric base, and a plurality of crosslinking compositions on the sensor.

Sensors in accordance with embodiments of the invention can be made manually, using the processes described above, or can be made using automated or semi-automated equipment. In some embodiments, a plurality of sensors can be made using automated or semi-automated equipment operating in a "batch" mode, wherein a batch of sensors are made at the same time, or in a continuous mode, wherein sensors are continuously produced.

In some embodiments, methods of making the subject sensors include depositing or forming one or more electrodes on the surface of the piezoelectric base. Deposition of the electrodes can be accomplished using any suitable method, including, e.g., photolithography techniques, vapor deposition techniques, electrode printing techniques, and the like.

In one preferred embodiment, a sensor comprises surface-associated compositions that are made from protein G and polyclonal antibodies, and comprises crosslinking compositions that are also made from protein G and polyclonal antibodies.

In another preferred embodiment, a sensor comprises surface-associated compositions that are made from protein A and polyclonal antibodies, and comprises crosslinking compositions that are also made from protein A and polyclonal antibodies.

In another preferred embodiment, a sensor comprises surface-associated compositions that are made from protein G and monoclonal antibodies, and comprises crosslinking compositions that are also made from protein G and monoclonal antibodies.

In another preferred embodiment, a sensor comprises surface-associated compositions that are made from protein A and monoclonal antibodies, and comprises crosslinking compositions that are also made from protein A and monoclonal antibodies.

Systems

Aspects of the invention include systems that can be used in connection with the subject sensors to carry out the methods described herein. Systems in accordance with embodiments of the invention include detection units that are configured to interact with a subject sensor, as well as peripheral components that find use in carrying out the subject methods.

In some embodiments, a system includes a detection unit that is configured to connect to one or more sensors. In some embodiments, a detection unit includes a connection feature or docking port that operatively connects a sensor to the detection unit. In some embodiments, the connection feature includes electrical leads and/or electrode contacts that are configured to establish an electrical connection between the detection unit and one or more features of the sensor. In some embodiments, a detection unit may include a plurality of connection features or docking ports, such that a plurality of sensors can be connected simultaneously to the detection unit. In some embodiments, a detection unit may include a number of docking ports ranging from 1 to 10, such as 2, 3, 4, 5, 6, 7, 8 or 9. In some embodiments, a sensor is permanently attached to the detection unit. In some embodiments, a detection unit may include a release component that is configured to dis-engage a sensor from the detection unit. For example, in some embodiments, a detection unit may include a button or a lever that can be used to dis-engage a sensor from the detection unit.

In some embodiments, a system includes one or more temperature control elements that are configured to control the temperature of one or more portions of the sensor and/or a sample this being contacted with the sensor. For example, in some embodiments, a system includes a temperature controller that is configured to maintain the sensor within a target temperature range. In some embodiments, a detection unit includes a temperature controller that is configured to maintain a sample, or a portion thereof, at a target temperature for analysis. Temperature control elements in accordance with embodiments of the device may include temperature blankets, resistive heaters, thermoelectric heaters or coolers, fans, and the like.

In some embodiments, a system includes an oscillator circuit that is configured to electrically connect to a sensor. The oscillator circuit is configured to drive the sensor at one or more frequencies, including but not limited to, a resonant frequency of the piezoelectric base material of the sensor. In certain embodiments, the oscillator circuit includes an automatic gain control (AGC) portion. Oscillator circuits in accordance with embodiments of the invention may include one or more resistors, capacitors and/or inductors, arranged in series and/or in parallel. Aspects of the automatic gain control portion of the oscillator circuit that can be measured include, but are not limited to, the voltage, resistance, admittance, impedance or conductance values of the circuit. In some embodiments, an oscillator circuit is a lever oscillator that is designed for use with liquid applications.

In some embodiments, a system includes a comparator/receiver component that is configured to receive a signal from a sensor, and is also configured to receive a signal from an oscillator circuit that is electrically connected to the sensor. The comparator/receiver component is configured to compare and measure one or more features of the signals that are received from the sensor and the oscillator circuit. The measured feature(s) of the sensor and the oscillator circuit can then be used to determine the concentration of the analyte that is present on the sensor.

In some embodiments, a system includes a frequency spectrum analyzer that is configured to measure one of more features of the sensor as a function of the oscillation frequency applied to the sensor. For example, in some embodiments, a frequency spectrum analyzer is configured to measure a change in the frequency, amplitude and/or frequency bandwidth of a waveform in the sensor as a function of the oscillation frequency that is applied to the sensor by the oscillator circuit. The data acquired by the frequency spectrum analyzer is recorded and analyzed by the system.

In some embodiments, a system includes a controller that is configured or adapted to control or operate one or more components of the subject systems. In some embodiments, the controller is in communication with one or more components of the system and is configured to control aspects of the system and/or execute one or more operations or functions of the system. In some embodiments, a system includes a processor and a computer-readable medium, which may include memory media and/or storage media. Applications and/or operating systems embodied as computer-readable instructions on computer-readable memory can be executed by the processor to provide some or all of the functionalities described herein, including by not limited to, carrying out one or more of the method steps described herein, acquiring and processing data obtained from the subject sensors and/or systems, and/or applying one or more algorithms or other manipulations to the data for analysis.

In some embodiments, a system includes a user interface, such as a graphical user interface (GUI), that is adapted or configured to receive input from a user. In some embodiments, a GUI is configured to display data or information to a user. In some embodiments, the subject systems include an indicator or readout screen that can be used to communicate information to a user. For example, in some embodiments, a system may include an indicator light that is illuminated when the system detects an analyte of interest in a sample above an established concentration threshold. In some embodiments, a readout screen is configured to display a list of one or more analytes that are detected in a sample.

Additional aspects of the subject systems may include, but are not limited to, analog to digital converters that are configured to convert one or more continuous physical quantities, such as a voltage measurement, to a digital number that represents the quantity's amplitude. Aspects of the subject systems also include data exchange features, such as, e.g., USB ports, Ethernet ports, or other data ports that are configured to establish a connection that can be used to exchange/transmit data between two or more components of the system. Aspects of the subject systems also include wireless transmission components, such as WiFi components, that are configured to wirelessly transmit data between two or more components of the system.

Aspects of the subject systems may also include computer processors, data storage, and/or database components that can be used to store and/or analyze data that is acquired by the subject systems. Such components can be physically connected to other components of the subject systems, such as, e.g., via a USB connection, or can be configured to wirelessly communicate with other components of the subject systems, e.g., via WiFi connection, or via the Internet. In some embodiments, computer processors, data storage and/or database components of the subject systems may be remotely located, e.g., may be located at a physical location that is different from the physical location of the sensor and/or the detection unit.

Aspects of the subject systems may also include power components, such as batteries and/or power cables that are configured to provide electrical power to the subject sensors and systems. Power components in accordance with embodiments of the invention may be modular and may be configured to be removeably coupled to the subject systems for purposes of providing power thereto, for example, one or more batteries or battery packs that are configured to be inserted into or otherwise coupled to the subject systems. In some embodiments, the subject systems include power cables that are configured to establish electrical contact with standard power outlets.

In some embodiments, the various features of the subject systems are formed into a single device that includes a housing formed from suitable materials, such as plastic, metal, glass or ceramic materials, and any combinations thereof. For example, in some embodiments, a detection unit is formed from a plastic housing, and various additional components of the system are located within the housing. In some embodiments, a system is formed into a single benchtop device that can be used to carry out the subject methods, as described further below. In some embodiments, a system is formed into a single, hand-held device that can be carried by a user.

In some embodiments, various features of the subject systems can be formed into two or more separate devices, and the devices can be configured to transmit data and/or operating parameters between one another. For example, in some embodiments, a sensor unit that includes a housing, a sensor, an oscillator circuit, a controller, and a processor is configured to interact with a detection unit that includes a housing, a processor, and a comparator/receiver component. In some embodiments, the sensor unit is configured to communicate wirelessly with the detection unit, while is some embodiments, the sensor unit may be connected to the detection unit via, e.g., a USB cable. In use, the sensor unit collects data from a sample and transmits the data to the detection unit, where the data is analyzed and evaluated to determine whether a target analyte is present in the sample. In some embodiments, the detection unit transmits data and/or operating parameters to the sensor unit.

In some embodiments, the subject systems include a plurality of sensor units that can be located at different locations, e.g., for environmental monitoring. For example, in some embodiments, a plurality of sensor units can be placed at various geographical locations, and can be used to monitor the presence of an analyte in a sample collected from each location. Data can be transmitted from the plurality of sensor units to one or more detection units, where the data is analyzed. In some embodiments, each of the sensor units may include a plurality of sensors, e.g., a sensor array, wherein each sensor is configured to detect a different target analyte, so that a sample can be analyzed, using the sensor array, for the presence of a plurality of target analytes. In certain embodiments, a system may include a "blank" sensor, or a negative control sensor, that is configured to provide a negative control for analysis. In some embodiments, a system may include a positive control sensor that is configured to provide a positive control for analysis.

Aspects of the subject systems may include activated carbon compositions that can be used to concentrate an analyte or antigen in a sample. Activated carbon compositions in accordance with embodiments of the invention include activated carbon particulates, granules, powders, filaments and nanotubes. In use, an activated carbon composition is contacted with a sample that contains an analyte of interest. The analyte is adsorbed onto the activated carbon composition, thereby creating a multi-valent composition that includes multiple analyte molecules that can bind to the molecules on the sensor. Accordingly, exposing a sample to an activated carbon composition can be used to concentrate the analyte onto the carbon composition, and thereby amplify the signal that is detected by the sensor. In some embodiments, an activated carbon composition is present on a surface of a sensor (i.e., is disposed on a surface of a sensor). In some embodiments, an activated carbon composition can be deposited on a surface of a sensor during a production process. For example, in some embodiments, an activated carbon composition is combined with one or more components to be deposited on a sensor surface (e.g., combined with a solution that comprises a plurality of surface compositions and/or crosslinking compositions) and deposited on the surface of the sensor. In some embodiments, an activated carbon composition can be deposited on a surface of a sensor after a production process. For example, in some embodiments, an activated carbon composition is deposited on a surface of a sensor after the surface-associated compositions and crosslinking compositions have been deposited.

Aspects of the subject systems may include secondary detection devices that are configured to detect and/or quantify one or more detectable labels or moieties that may be present on the compositions of the subject sensors. Such secondary detection devices include, but are not limited to, spectrophotometers, fluoroscopes, ellipsometers, and the like. After a subject sensor is contacted with a sample that contains a target analyte, the analyte binds to the compositions on the sensor and creates a crosslinked network of molecules. The presence of the analyte on the sensor is detected by the subject systems, as described above. For purposes of verifying the results obtained from the sensor, the subject secondary detection devices can be used to confirm the presence of the analyte in the sample by further analyzing the sensor.

When a crosslinked network of molecules is formed on the sensor as a result of a target analyte binding to the sensor, the surface-associated compositions and crosslinking compositions are bound in place on the sensor. As described above, in some embodiments, the compositions may include a detectable label. The subject secondary detection devices can be used to quantify the amount of the detectable label that is present on the sensor, thereby verifying the results obtained from the sensor. In certain embodiments, a sensor may include a cap element that is configured to be removeably coupled to the sensor. The cap is configured to be removed from the sensor so that the sensor can be contacted with a sample. Following detection of an analyte in the sample, the cap can be replaced in order to protect the sensor tip. The sensor can then be analyzed by a secondary detection device to confirm the results of the sample analysis. For example, in some embodiments, the cap can be removed from the tip of a used sensor, and the used sensor can be analyzed with a secondary detection device to confirm the results of the analysis by confirming the amount of a detectable label that is present on the sensor, thus indicating the amount of the analyte that was present in the sample.

Figure 5:
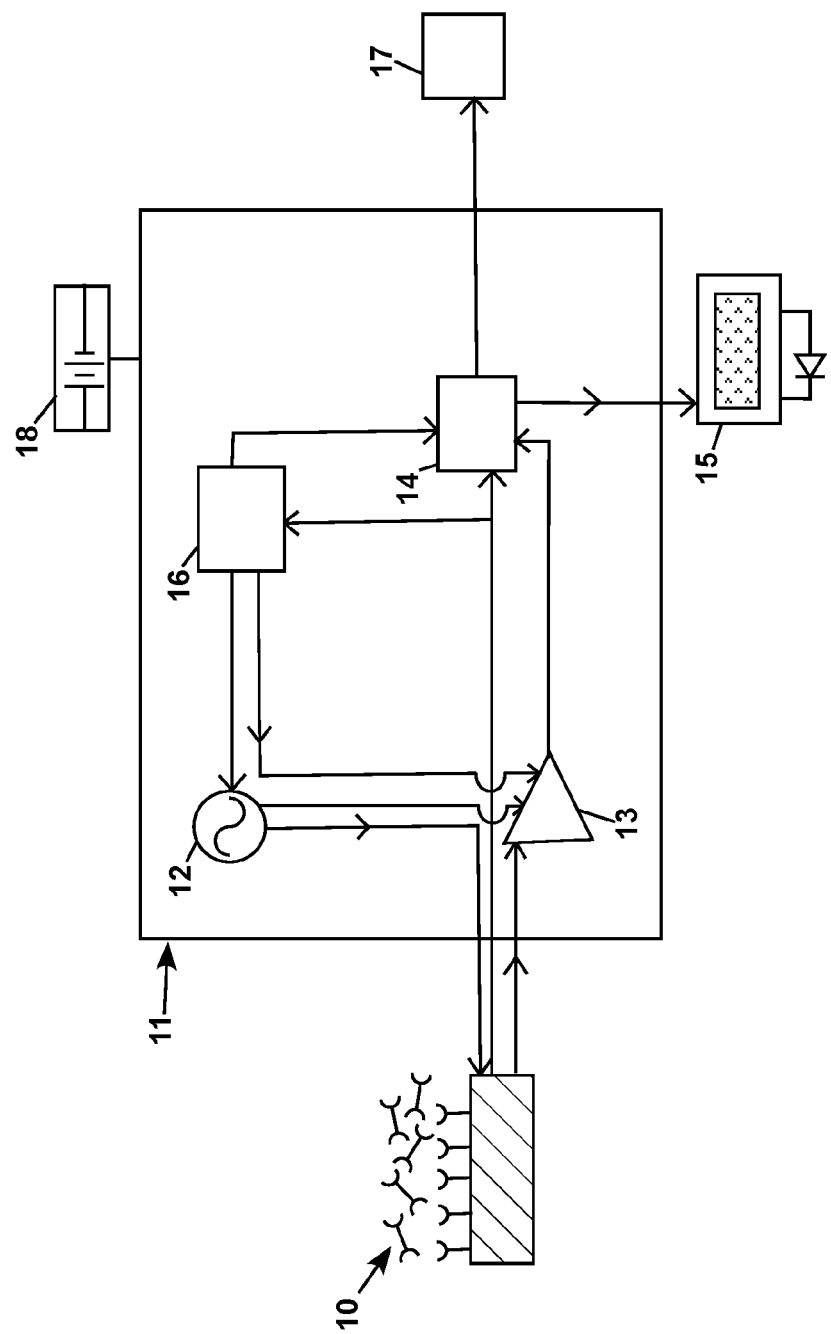
FIG. 5 is a diagram showing a schematic representation of a subject sensor electrically connected to a system that includes electrical circuitry for driving the sensor and detecting data from the sensor.

FIG. 5 shows a schematic representation of a subject sensor 10 that is electrically connected to a system 11 that includes electrical circuitry for driving the sensor and collecting data from the sensor. The system 11 includes an oscillator 12 that is configured to drive the sensor 10 at a plurality of different frequencies. The system 11 also includes a comparator/receiver 13 that is configured to receive one or more signals from the oscillator 12 and one or more signals from the sensor 10, and to compare the received signals to each other. The system 11 also includes a processor 14 that includes a computer readable medium that is configured to receive data from the sensor 10 and from the comparator/receiver 13, and to process, store and/or transmit the data as needed. The system 11 also includes an indicator/readout screen 15 that is configured to receive a signal from the processor 14 and to display that signal to a user. The system 11 also includes a controller 16 that is configured to control one or more portions of a test procedure. The system 11 also includes a data transmission component 17 that is configured to transmit data outside the system 11. Finally, the system 11 also includes a power supply 18 that is configured to supply power to the system 11.

Figure 6:
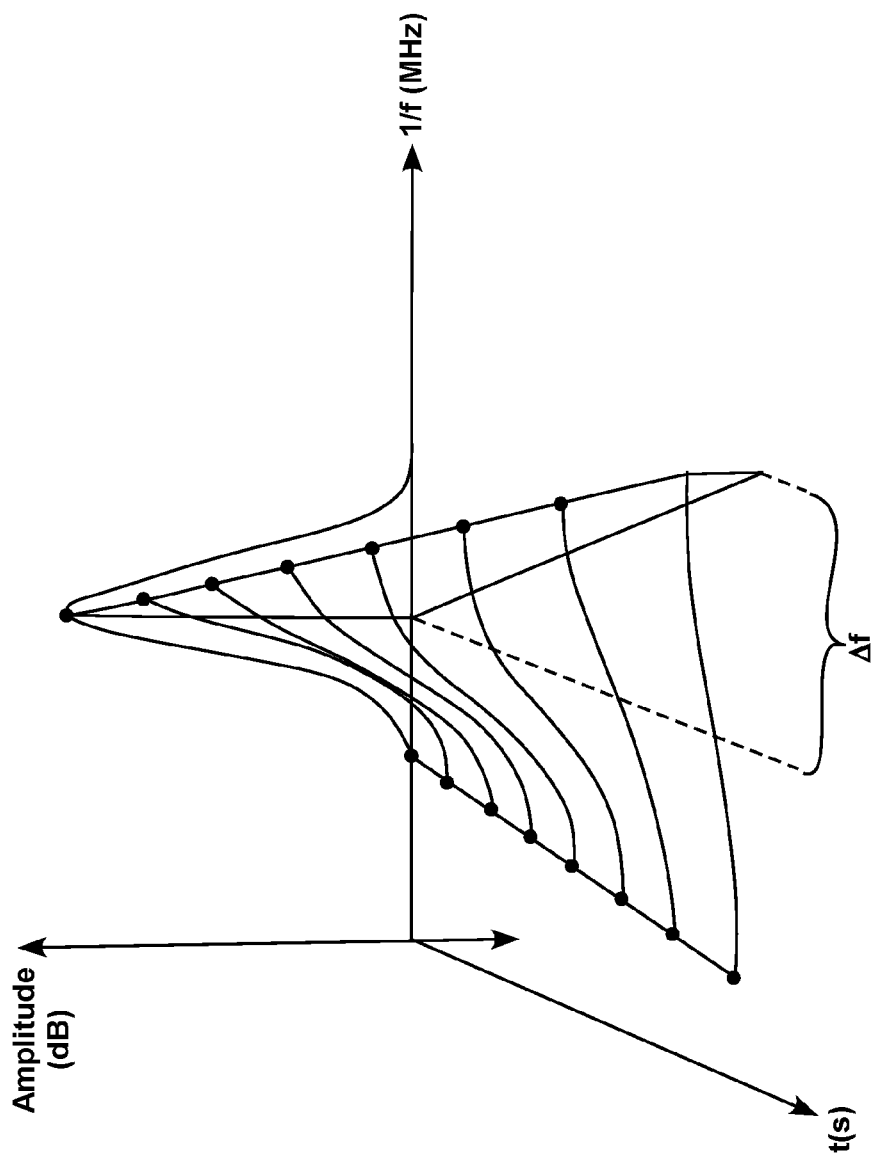
FIG. 6 is a diagram showing a schematic representation of a signal received from a subject sensor as a function of time after the sensor has been contacted with a sample containing an analyte.

FIG. 6 shows a schematic representation of a signal received from a subject sensor as a function of time after the sensor has been contacted with a sample containing an analyte. The signal is plotted to show the amplitude (dB) as a function of both time (s) and frequency (MHz). As shown, the change in frequency ($\Delta f$) can be measured as a function of time after a sample containing an analyte is contacted with the sensor.

Figure 7:
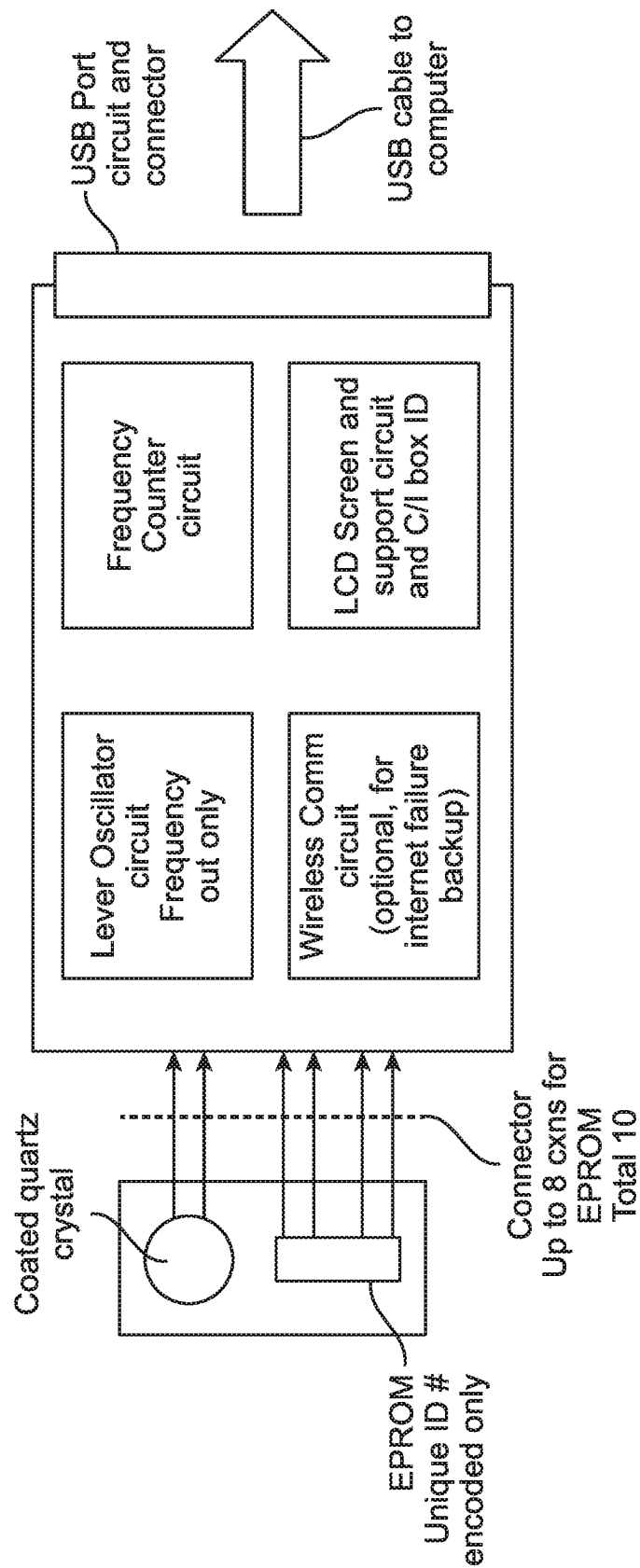
FIG. 7 is a schematic illustration of a sensor and a detection component.
Figure 8:
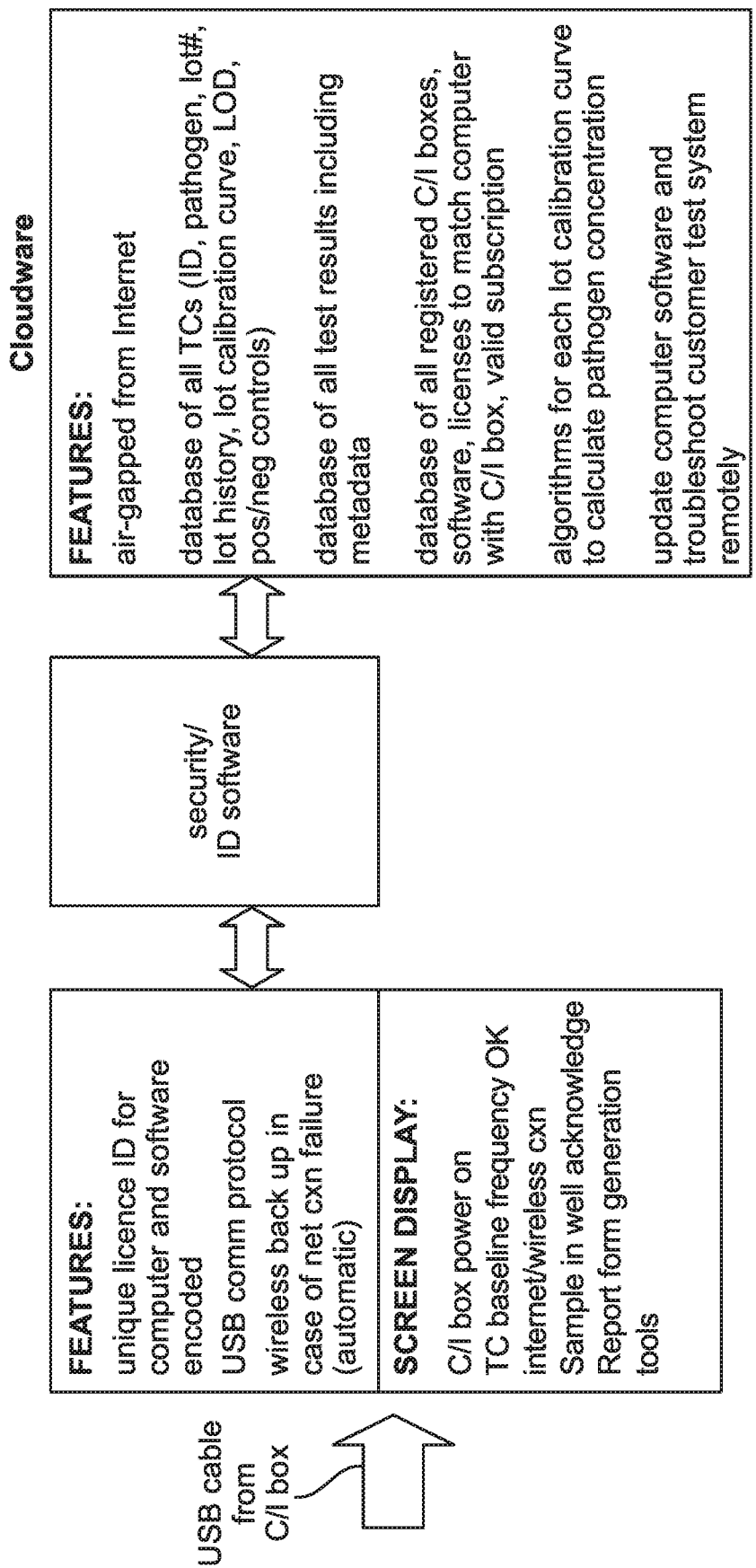
FIG. 8 is an illustration of that shows the flow of information between various components of a system.

Depicted in FIG. 7 is a system that includes a sensor and a detection component with a data exchange feature that can be connected to a computer. As shown, the sensor includes a piezoelectric base (coated quartz crystal) and a computer-readable medium (EPROM). The depicted detection component includes a lever oscillator circuit, frequency counter circuit, wireless communication circuit, LCD screen and support circuit, and a USB port circuit and connector for communicating with a computer. FIG. 8 depicts the features and functionality of a computer that is connected to the system depicted in FIG. 7. As shown in FIG. 8, the computer is connected to the Internet, and can interface with cloud-ware to access various types of information, including but not limited to, a database of all sensors (test cartridges, TCs), test results, data subscription registration information, test algorithms, calibration information, as well as computer software updates.

Methods of Use

Methods in accordance with embodiments of the invention may be used to detect an analyte in a sample. The subject methods involve contacting a sensor, as described above, with a sample that is suspected of containing an analyte of interest, and detecting the presence or absence of the analyte in the sample.

An analyte that is present in a sample binds to the compositions that are present on the sensor and forms crosslinks between the compositions. This crosslinking changes the mechanical properties of the sensor (e.g., changes the dynamic modulus of the sensor). A voltage or current is applied to an oscillator circuit that is electrically connected to the sensor. The oscillator circuit drives the sensor at one or more frequencies, and changes in the mechanical properties of the sensor resulting from crosslinking of the surface-associated compositions and crosslinking compositions are detected. In some embodiments, changes in the sensor and/or the parameters of the oscillator circuit are measured as a function of time. The magnitude and type of changes in the sensor and/or oscillator circuit are used to determine the concentration of the analyte in the sample.

Methods in accordance with embodiments of the invention can be used to analyze any sample that contains, or may contain, an analyte of interest. In some embodiments, a sample is a liquid sample. Liquid samples that are amenable to analysis with the subject sensors and systems include aqueous as well as non-aqueous liquids. In some embodiments, a liquid sample may be a bodily fluid, including but not limited to: amniotic fluid, aqueous or vitreous humor, bile, blood, breast milk, cerebrospinal fluid, cerumen (ear wax), lymphatic fluid, mucus, pleural fluid, pus, saliva, semen, sputum, synovial fluid, sweat, tears, urine, or vaginal fluid or secretions. In some embodiments, a sample is a non-liquid sample, e.g., a solid or semi-solid composition.

In some embodiments, the subject methods do not involve preparing a sample for analysis. For example, in certain embodiments, the subject methods involve contacting a sample with a subject sensor without preparing or modifying the liquid sample in any way. In some embodiments, the subject methods involve contacting a body fluid with a subject sensor without preparing or modifying the body fluid in any way.

In some embodiments, the subject methods involve preparing a sample for analysis by combining the sample with one or more reagents. For example, in some embodiments, a liquid sample may be diluted by combining the sample with an appropriate diluent. Similarly, in some embodiments, a solid or semi-solid sample may be combined with a liquid in order to create a liquid sample that includes the solid or semi-solid sample either in suspension or in solution. In certain embodiments, other reagents may be added to a sample in order to facilitate the analysis of an analyte in the sample, such as emulsifiers, chelating reagents, and the like. In some embodiments, an activated carbon composition may be combined with the sample in order to collect one or more molecules of the analyte on the surface of the activated carbon composition. In certain embodiments, the activated carbon composition includes a carbon nanotube.

In some embodiments, the methods involve mixing a liquid sample with one or more reagents and/or diluents to prepare the sample for analysis. For example, in some embodiments, a liquid sample may be mixed with a diluent to reduce the concentration of an analyte in the sample. Various dilution techniques can be used in conjunction with the subject methods, including but not limited to, diluting a sample by a specific dilution factor, or performing a serial dilution of the sample.

Contacting a sensor with a sample can be accomplished using any suitable technique. For example, in some embodiments, a sensor may be immersed in a liquid sample, e.g., a sensor can be immersed in a body of water, or immersed in a container that contains a liquid sample of interest. In some embodiments, a liquid sample can be collected in a suitable container, and a sensor is then inserted into the container to contact the sample. In certain embodiments, a container for sample collection may be configured to be sealed after a sample is placed inside in order to maintain sterility of the sample or to prevent adulteration of the sample, and also to protect a technician or operator from contacting the sample. In certain embodiments, a sensor may be configured to fluidly connect to a container that holds a liquid sample, thereby contacting the liquid sample with the sensor. In some embodiments, a liquid sample can be collected using a suitable device, e.g., a pipette or micropipette, and the liquid sample can then be deposited directly onto the sensor.

In some embodiments, the methods involve contacting a substantially dry sensor with a sample to be analyzed. In such embodiments, the sample hydrates a surface of the sensor. In some embodiments, the methods involve hydrating a surface of sensor with a liquid that does not contain a target analyte (e.g., a saline solution), and then contacting the sensor with a sample to be analyzed. For example, in certain embodiments, the methods involve contacting a surface of a sensor with a saline solution to hydrate the sensor, and then contacting the surface of the sensor with a sample that contains (or is suspected of containing) a target analyte.

Aspects of the subject methods involve driving a sensor at one or more frequencies using an oscillator circuit, as described above, and measuring one or more parameters of the sensor and/or the oscillator circuit as a function of time at each frequency after the sensor has been contacted with a sample. In some embodiments, the subject methods involve measuring the frequency of a waveform that is generated in the sensor in response to an input voltage or current that is applied to the sensor by an oscillator circuit. In some embodiments, the subject methods involve measuring the amplitude of the waveform in the sensor. In certain embodiments, the subject methods involve measuring the frequency bandwidth, or Q-factor, of the waveform in the sensor. Any combination of the frequency, amplitude and/or frequency bandwidth of a waveform in the sensor may be measured and used in the subject methods for determining the concentration of an analyte in a sample that is applied to the sensor. In certain embodiments, one or more of the frequency, amplitude or frequency bandwidth of a waveform in the sensor is measured as a function of time. In some embodiments, one or more even or odd harmonics of a fundamental test frequency are measured.

Aspects of the subject methods involve measuring one or more parameters of an oscillator circuit that drives the sensor at one or more frequencies. As reviewed above, oscillator circuits in accordance with embodiments of the invention may include an automatic gain control portion, and may include one or more resistors, capacitors and/or inductors, arranged in series and/or in parallel. Aspects of the subject methods may include measuring a voltage, resistance, admittance, impedance or conductance value of an oscillator circuit, or any portion thereof, such as an automatic gain control portion of the oscillator circuit. Any combination of the voltage, resistance, admittance, impedance or conductance values of the oscillator circuit can be measured and used in the subject methods for determining a concentration of an analyte in a sample that is applied to the sensor. In some embodiments, one or more of the voltage, resistance, admittance, impedance or conductance values of the oscillator circuit is measured as a function of time.

In some embodiments, the subject methods involve applying a driving voltage or current (e.g., an alternating current) to a sensor for a period of time, and then measuring one or more parameters of the sensor as a function of time once the driving voltage or current is shut off. In such embodiments, the decay rate or dissipation of energy in the sensor can be measured as a function of time, and can be used to determine the concentration of an analyte in the sample that was applied to the sensor.

In some embodiments, the subject methods involve using a frequency spectrum analyzer to analyze one or more attributes of a waveform (e.g., the frequency, amplitude and/or frequency bandwidth) generated in the piezoelectric base as a function of one or more electronic signals that are applied to the sensor by an oscillator circuit. For example, in some embodiments, an oscillator circuit is used to drive the sensor at a plurality of different frequencies, and a frequency spectrum analyzer is used to analyze one or more attributes of a waveform that is generated in the sensor in response to each input frequency. In some embodiments, a frequency spectrum analyzer is used to analyze changes in a waveform that is generated in the sensor as a function of time.

In some embodiments, the subject methods can be used to obtain results from a sample in a short period of time. For example, in some embodiments, the subject methods involve contacting a sensor with a sample, and determining the concentration of an analyte in the sample in a period of time ranging from 5 seconds or less, up to 5 minutes, such as 1, 2, 3, 4, 5, 10, 15, 20, 25, 30, 35, 40, 45, 50 or 55 seconds, or up to 1, 1.5, 2, 2.5, 3, 3.5, 4, or 4.5 minutes.

Methods in accordance with embodiments of the invention include both qualitative and quantitative analyte detection. As such, in some embodiments, the subject methods involve determining whether an analyte is present in a sample at a concentration that is above or below a target, or threshold, concentration. In some embodiments, a threshold concentration for a particular analyte may range from 0.1 to 1,000 ppm, such as 0.5, 1, 10, 20, 30, 40, 50, 60, 70, 80, 90, 100, 200, 300, 400, 500, 600, 700, 800 or 900 ppm. In some embodiments, a threshold concentration for a particular analyte may range from 1 to 1,000 colony forming units (CFU)/mL, such as 10, 20, 30, 40, 50, 60, 70, 80, 90, 100, 200, 300, 400, 500, 600, 700, 800 or 900 CFU/mL.

In some embodiments, the subject methods involve quantitatively determining the concentration of an analyte in a sample. In certain embodiments, the methods involving comparing a result obtained from a sensor and/or an oscillator circuit to one or more calibration values that can be used to quantitatively determine a concentration of an analyte in a sample. In some embodiments, the subject methods involve applying one or more calculations or algorithms to the results in order to quantitatively determine a concentration of an analyte in a sample. In some embodiments, the subject methods involve comparing a plurality of data obtained from a sensor and/or an oscillator circuit to an analyte signature in order to determine whether the analyte is present in the sample, and/or to quantitatively determine the concentration of the analyte in the sample.

In some embodiments, the subject methods involve verifying a result obtained from a sensor by using a secondary detection device. As described above, in some embodiments, a sensor may include a surface-associated composition and/or a crosslinking composition that includes a detectable label or moiety. When an analyte crosslinks the surface-associated compositions and crosslinking compositions on the sensor, the compositions are bound in place on the sensor. As such, in certain embodiments, the subject methods involve detecting and/or quantifying a detectable label or moiety on the sensor using a secondary detection device. For example, in some embodiments, the subject methods involve placing a used sensor in a secondary detection device, and using the secondary detection device to quantify the amount of a detectable label that is present on the sensor. Quantification of the detectable label on the sensor is used to verify the results that were previously obtained from the sensor.

In some embodiments, the subject methods involve monitoring the presence of an analyte in a plurality of samples that are collected from different geographical locations. For example, in some embodiments, the subject methods involve placing a plurality of sensors at different geographical locations, wherein each sensor is configured to contact a sample at each geographical location. Each of the sensors analyzes a sample from the geographical location where it is located, and the results are transmitted to a detection unit for analysis. The results that are obtained from each sensor can then be used to determine the presence or absence of the analyte over a specific geographical area.

For example, in some embodiments, a plurality of sensors can be placed at different geographical locations in a body of water, such as a lake, stream or reservoir. Each sensor analyzes a sample from its geographic location and transmits the results to a detection unit for analysis. The results are then used to determine the presence or absence of the analyte in various geographic portions of the body of water. Such methods find use is detecting, e.g., contamination of a body of water with pollutants or toxins, and more specifically, determining the specific geographic portions of a body of water that are contaminated with a particular pollutant or toxin.

Figure 2:
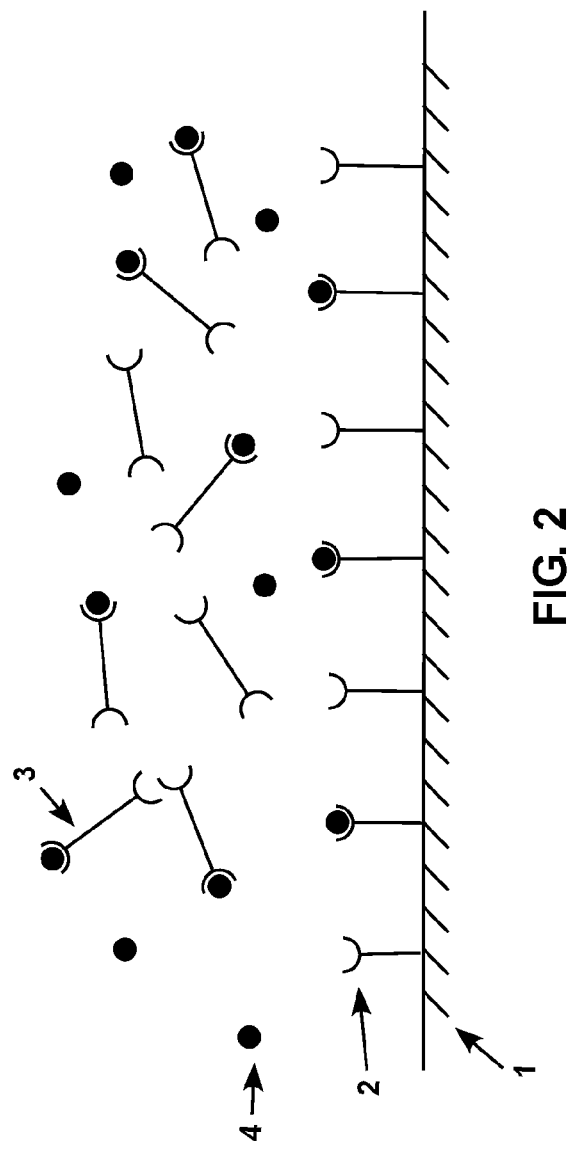
FIG. 2 is a diagram showing a schematic representation of a subject sensor with a plurality of surface-associated compositions and crosslinking compositions thereon shortly after the sensor has been contacted with a sample containing an analyte.

FIG. 2 depicts the same sensor as depicted in FIG. 1 shortly after a sample containing an analyte 4 has been contacted with the sensor. As shown in FIG. 2, the analyte 4 binds to the surface-associated compositions 2 as well as the crosslinking compositions 3.

Figure 3:
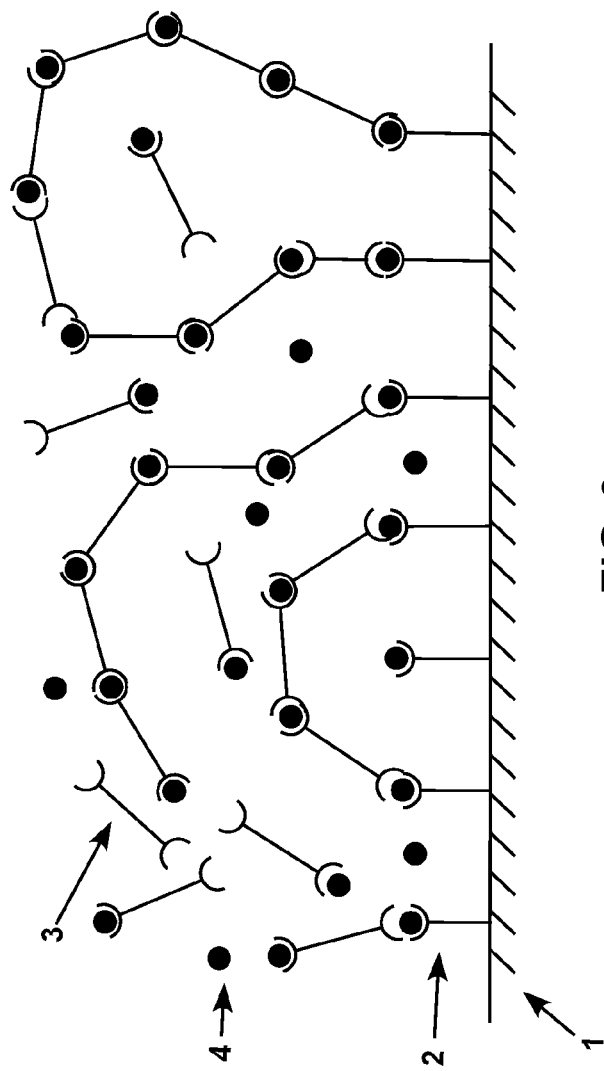
FIG. 3 is a diagram showing a schematic representation of a subject sensor with a plurality of surface-associated compositions and crosslinking compositions thereon after the sensor has been contacted with a sample containing an analyte.

FIG. 3 depicts the same sensor as depicted in FIG. 1 and FIG. 2 at a longer time after a sample containing an analyte 4 has been contacted with the sensor. As shown in FIG. 3, the analyte 4 is bound to the surface-associated compositions 2 as well as the crosslinking compositions 3, and the presence of the analyte 4 has resulted in the formation of crosslinks between the surface-associated compositions 2 and the crosslinking compositions 3.

Figure 4:
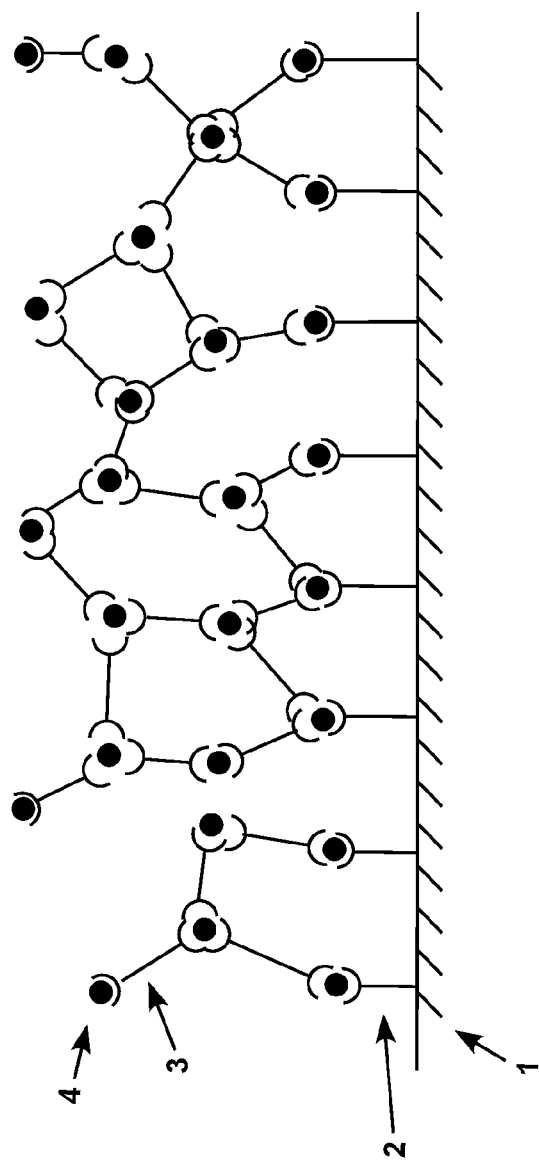
FIG. 4 is a diagram showing a schematic representation of a subject sensor with a plurality of surface-associated compositions and crosslinking compositions thereon after the sensor has been contacted with a sample containing an analyte.

FIG. 4 depicts the same sensor as depicted in FIGS. 1-3 at an even longer time after a sample containing an analyte 6 has been contacted with the sensor. As shown in FIG. 4, the analyte 4 is bound to the surface-associated compositions 2 as well as the crosslinking compositions 3, and the presence of the analyte 4 has resulted in the formation of extensive crosslinks between the surface-associated compositions 2 and the crosslinking compositions 3.

Kits

Also provided are kits that at least include the subject systems and devices or components thereof, e.g., as described above, and instructions for how to use the devices in the detection and quantification of one or more target analytes in a sample. In some embodiments, a kit includes two or more sensors packaged in a sterile package. In some embodiments, the sensors in the kit are configured to detect different analytes.

In some embodiments, a kit includes one or more sensors that include a detectable label or moiety, and the kit includes a reagent that is configured to facilitate the detection of the detectable label with a secondary detection system. In some embodiments, a kit includes an activated carbon composition. In certain embodiments, a kit includes an activated carbon composition that includes a carbon nanotube.

In some embodiments, a kit includes one or more sample collection devices. Sample collection devices in accordance with embodiments of the invention may include test tubes, cups, beakers, pipettes, dipsticks, swabs, spatulas, or other devices configured to collect at least a small quantity of a sample. In some embodiments, the sample collection devices may include lids and/or caps for the devices, as well as suitable storage containers, e.g., plastic storage bags or other packaging that can be used to store and/or transport the sample collection device without contaminating the sample. Sample collection devices in accordance with embodiments of the invention may be configured to collect a liquid sample, a solid sample, or a semi-solid sample. In some embodiments, a sample collection device may be configured to collect a solid or semi-solid sample and to process the sample by crushing or pulverizing it to facilitate mixing the sample with a liquid. Accordingly, the subject sample collection devices may also include implements that are configured for mixing a solid or semi-solid sample with a liquid.

The instructions for using the systems and devices as discussed above are generally recorded on a suitable recording medium. For example, the instructions may be printed on a substrate, such as paper or plastic, etc. As such, the instructions may be present in the kits as a package insert, in the labeling of the container of the kit or components thereof (i.e. associated with the packaging or sub-packaging) etc. In other embodiments, the instructions are present as an electronic storage data file present on a suitable computer-readable storage medium, e.g., a digital storage medium, e.g., a portable flash drive, a CD-ROM, a diskette, etc. The instructions may take any form, including complete instructions for how to use the systems and devices, or as a website address with which instructions posted on the Internet may be accessed.

EXAMPLES

Example 1: Detection of Viral Marker Protein Using Delta Frequency Measurement Only AT-cut quartz crystals with a fundamental resonance frequency of 10 MHz (ICM, Oklahoma City, Okla.) were cleaned by soaking in 1M NaOH for one hour. The crystals were rinsed with distilled water and soaked for one hour in 1M HCl, then rinsed with distilled water, rinsed with 70% isopropyl alcohol, and allowed to air dry. After drying, 100 microliters of a 1 mg/mL solution of recombinant protein G (BioVision, Inc., Milpitas, Calif., Catalog No. 6512) were applied to the crystal surfaces and allowed to air dry. 100 microliters of a 0.010 mg/mL solution of polyclonal rabbit anti-ZEBOV VP40 antibody (Zaire strain of Ebola virus, IBT Bioservices, Gaithersburg, Md., Catalog No. 0301-010) were then applied on top of the dried protein G layer and allowed to air dry.

Application of the protein G and polyclonal antibody solutions to the crystal created a plurality of surface-associated compositions that were stably associated with the surface of the quartz crystal, each surface-associated composition including a protein G molecule that was adsorbed to the crystal surface, and a polyclonal antibody that was bound to the immunoglobulin binding domain of the protein G molecule. Application of the protein G and polyclonal antibody solutions to the crystal also created a plurality of crosslinking compositions, each including one protein G molecule and two polyclonal antibodies, with each polyclonal antibody bound to an immunoglobulin binding domain of the protein G molecule.

A sensor with the above-described compositions formed thereon was operatively connected to a system including a lever oscillator circuit and a frequency counter, and a baseline frequency of the sensor was recorded. The sensor was contacted with 100 microliters of saline solution, and the change in frequency over time was recorded. A second sensor was operatively connected to the system, and the baseline frequency of the second sensor was recorded. The second sensor was contacted with 100 microliters of a 0.01 mg/mL solution of recombinant ZEBOV VP40 matrix protein (Zaire strain of Ebola virus, IBT Bioservices, Gaithersburg, Md., Catalog No. 0564-01), and the change in frequency over time was recorded. These steps were repeated using a porcine gelatin solution (1 mg/mL) as a control instead of the recombinant ZEBOV VP40 matrix protein solution.

Both the saline solution and porcine gelatin solution controls demonstrated a mean change in frequency of 1.86±0.54 kHz (n=22) within 5 seconds of applying the solution to the sensor. The sensor to which the rZEBOV solution was applied demonstrated a mean change in frequency of 9.98±0.47 kHz (n=10) within 5 seconds of applying the solution to the sensor. Based on the observed change in frequency of the sensor, the rZEBOV solution was distinguished from the control solutions within 5 seconds. As evidenced by the results from the porcine gelatin control solution, the sensor was specific for the rZEBOV protein, and did not generate a false positive signal when exposed to the porcine gelatin solution.

Example 2: Detection of Viral Marker Protein Using Delta Frequency Measurement Only AT-cut quartz crystals with a fundamental resonance frequency of 10 MHz (ICM, Oklahoma City, Okla.) were cleaned by soaking in 1M NaOH for one hour. The crystals were rinsed with distilled water and soaked for one hour in 1M HCl, then rinsed with distilled water, rinsed with 70% isopropyl alcohol, and allowed to air dry. After drying, 100 microliters of a 1 mg/mL solution of recombinant protein G (BioVision, Inc., Milpitas, Calif., Catalog No. 6512) were applied to the crystal surfaces and allowed to air dry. 100 microliters of a 0.010 mg/mL solution of polyclonal rabbit anti-ZEBOV GP antibody (Zaire strain of Ebola virus, IBT Bioservices, Gaithersburg, Md., Catalog No. 0301-015) was then applied on top of the dried protein G layer and allowed to air dry.

Application of the protein G and polyclonal antibody solutions to the crystal created a plurality of surface-associated compositions that were stably associated with the surface of the quartz crystal, each surface-associated composition including a protein G molecule that was adsorbed to the crystal surface, and a polyclonal antibody that was bound to the immunoglobulin binding domain of the protein G molecule. Application of the protein G and polyclonal antibody solutions to the crystal also created a plurality of crosslinking compositions, each including one protein G molecule and two polyclonal antibodies, with each polyclonal antibody bound to an immunoglobulin binding domain of the protein G molecule.

A sensor with the above-described compositions formed thereon was operatively connected to a system including a lever oscillator circuit and a frequency counter, and a baseline frequency of the sensor was recorded. The sensor was contacted with 100 microliters of saline solution, and the change in frequency over time was recorded. A second sensor was operatively connected to the system, and the baseline frequency of the second sensor was recorded. The second sensor was contacted with 100 microliters of a 0.01 mg/mL solution and a 0.001 mg/mL solution of recombinant EBOV rGPdTM protein (Zaire strain of Ebola virus, IBT Bioservices, Gaithersburg, Md., Catalog No. 0501-015), and the change in frequency over time was recorded. These steps were repeated using a porcine gelatin solution (Sigma Aldrich, 1 mg/mL, Catalog No. G2500) as a control instead of the recombinant EBOV rGPdTM protein solution.

Both the saline solution and porcine gelatin solution controls demonstrated a mean change in frequency of 1.86±0.54 kHz (n=22) within 5 seconds of applying the solution to the sensor. The sensors to which the 0.01 mg/mL solution of recombinant EBOV rGPdTM protein solution was applied demonstrated a mean change in frequency of 12.1±0.83 kHz (n=9). The sensors to which the 0.001 mg/mL solution of recombinant EBOV rGPdTM protein solution was applied demonstrated a mean change in frequency of 12.0±0.71 kHz (n=8). Based on the observed change in frequency of the sensor, the recombinant EBOV rGPdTM protein solutions were both distinguished from the control solution within 5 seconds. As evidenced by the results from the porcine gelatin control solution, the sensors were specific for the recombinant EBOV rGPdTM protein, and did not generate a false positive signal when exposed to the porcine gelatin solution.

Figure 10:
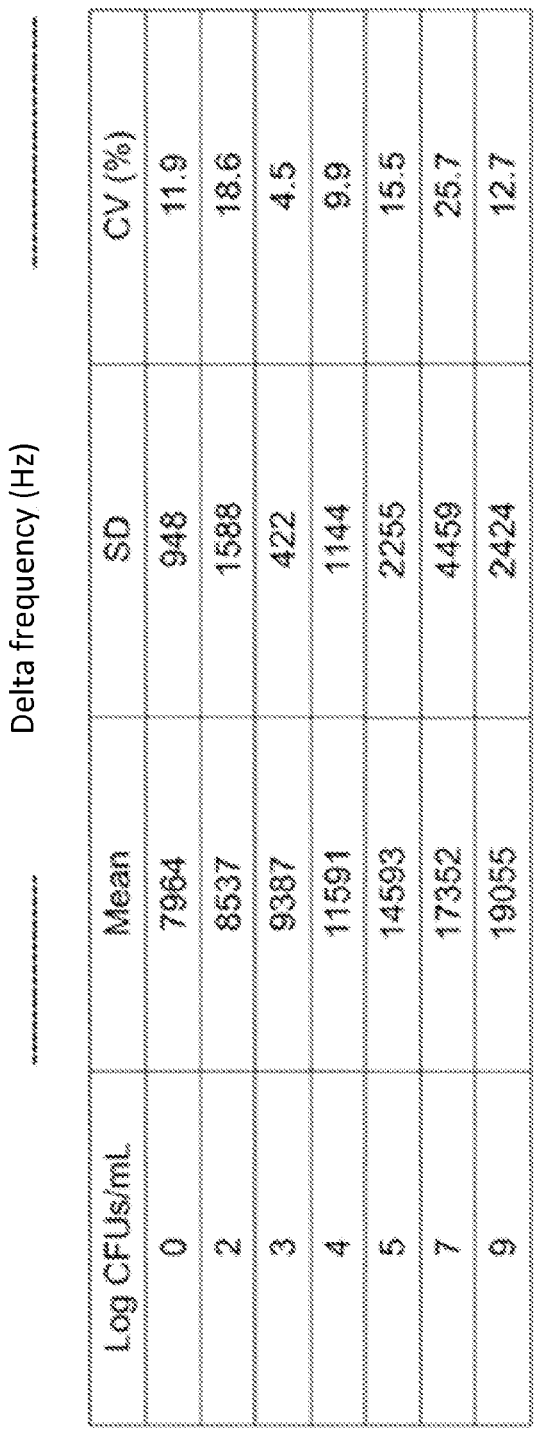
FIG. 10 is a table showing Log CFUs/mL and delta frequency response (mean, standard deviation (SD) and coefficient of variation (CV %)) for the data provided in FIG. 9.

Example 3: Determination of Delta Frequency Response from Monoclonal Antibody/Protein G Sensor as a Function of *Salmonella heidelberg* Concentration Sensors were made as described above by depositing 100 uL of a protein G solution (0.5 mg/mL, BioVision, Inc., Catalog No. 6510) on the surface of a piezoelectric base and allowing the solution to dry at 30° C. with circulating air, then depositing 100 uL of anti-*Salmonella heidelberg* (SH) murine monoclonal antibody solution (Cusabio, 10 ug/mL, Catalog No. CSB-PA472744YA01SWQ) on the piezoelectric base and allowing the solution to dry at 30° C. with circulating air. A *Salmonella heidelberg* control solution (UC Davis WIFSS, *S. Heidelberg* Strain #10) was diluted to prepare test solutions with Log CFU/mL values ranging from 0 to 9, as indicated in FIG. 10.

Figure 9:
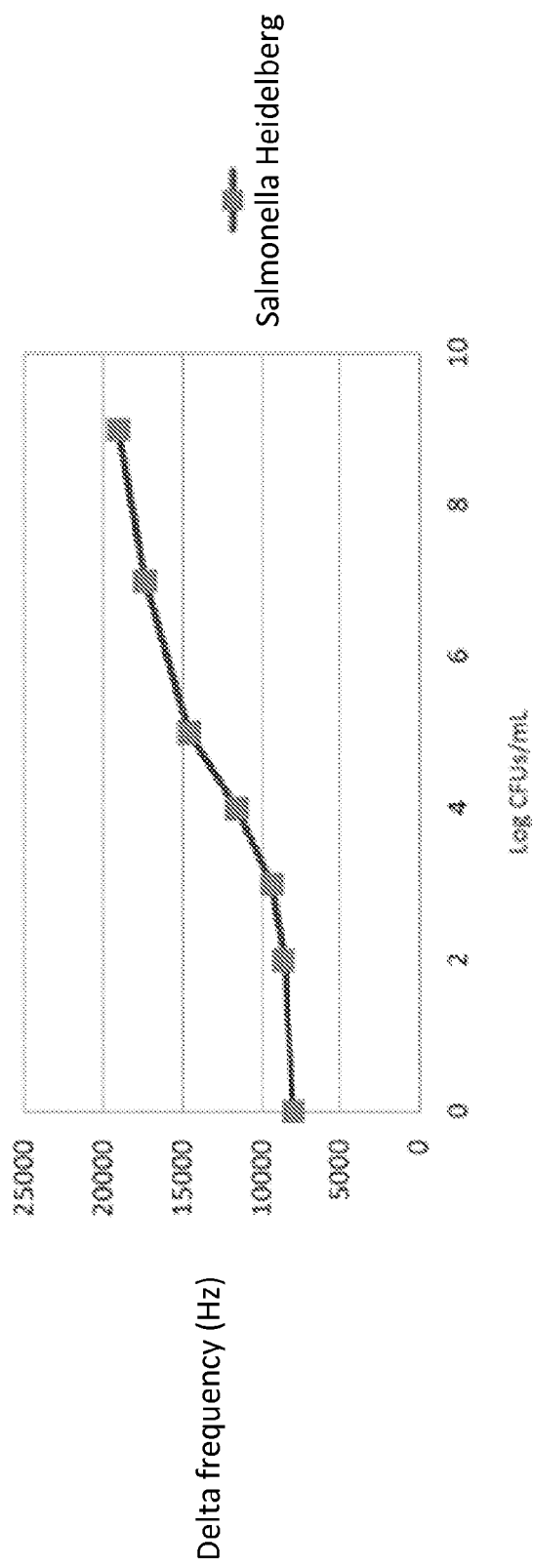
FIG. 9 is a graph showing delta frequency response of as a function of concentration of *Salmonella heidelberg*.

Each sensor was operatively connected to a system including a lever oscillator circuit and a frequency counter, and a baseline frequency of the sensor was recorded. The sensor was contacted with 100 microliters of test solution, and the change in frequency over time was recorded. Four sensors were tested at each indicated concentration, and the data are provided in FIGS. 9 and 10. A graph of delta frequency (Hz) v. Log concentration was prepared for use as a calibration curve to quantitatively analyze a test sample with an unknown concentration of SH. The correlation coefficient of the data was determined to be 0.9645, and the $R^2$ value was determined to be 0.9302.

Example 4: Analysis of Monoclonal Antibody/Protein C Sensor Reaction Time

Sensors were made as described above by depositing 100 uL of a protein G solution (0.5 mg/mL, BioVision, Inc., Catalog No. 6510) on the surface of a piezoelectric base and allowing the solution to dry at 30° C. with circulating air, then depositing 100 uL of anti-*Salmonella heidelberg* (SH) murine monoclonal antibody solution (Cusabio, 10 ug/mL, Catalog No. CSB-PA472744YA01SWQ) on the piezoelectric base and allowing the solution to dry at 30° C. with circulating air. A *Salmonella heidelberg* control solution (UC Davis WIFSS, *S. Heidelberg* Strain #10) was diluted to prepare test solutions with concentrations of $10^3$ CFUs/mL and $10^7$ CFUs/mL.

Figure 11:
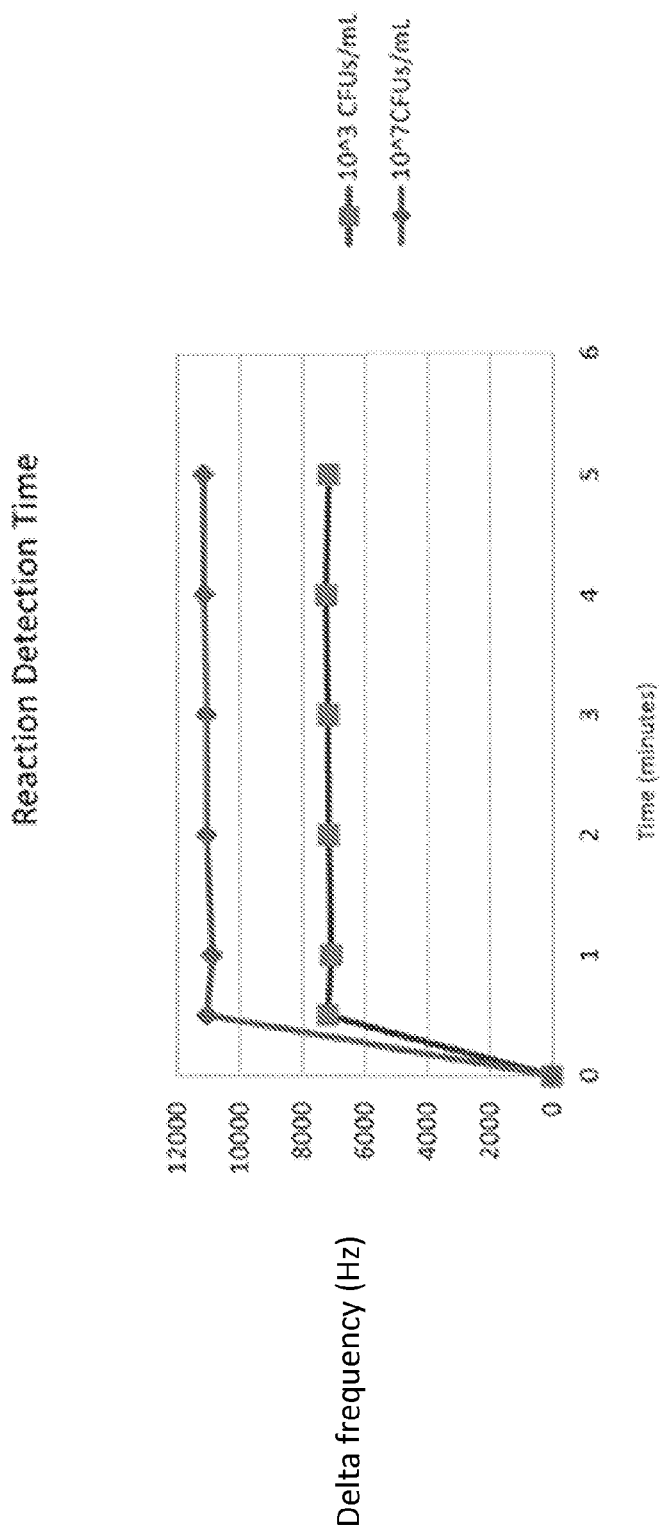
FIG. 11 is a graph showing delta frequency response as a function of time for two *Salmonella heidelberg* test solutions having different concentrations.
Figure 12:
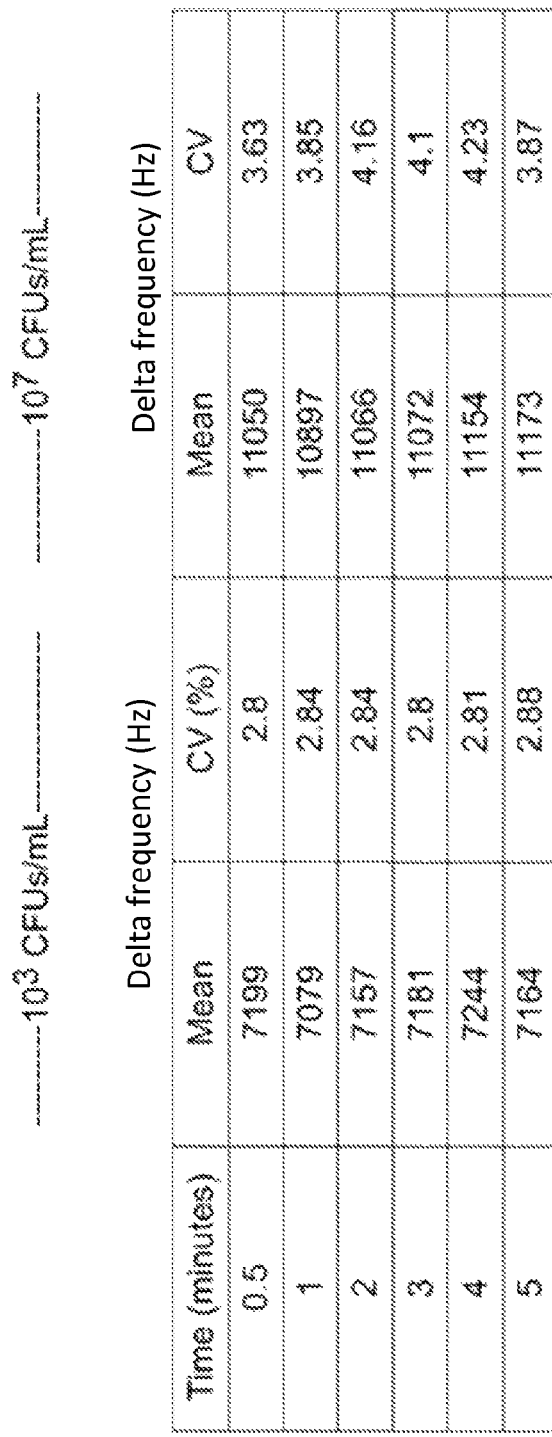
FIG. 12 is a table showing time in minutes, and the corresponding delta frequency mean and CV % values for test solutions having two different concentrations of *Salmonella heidelberg*.

Each sensor was operatively connected to a system including a lever oscillator circuit and a frequency counter, and a baseline frequency of the sensor was recorded. The sensor was contacted with 100 microliters of test solution, and the change in frequency over time was recorded. Five sensors were tested at each indicated concentration and time point, and the data are provided in FIGS. 11 and 12. The data demonstrate that the signal from both concentration levels tested reached a plateau value by the thirty second time point, and that a concentration of as low as $10^3$ CFUs/mL could be detected in 30 seconds.

Example 5: Analysis of Polyclonal Antibody/Protein a Sensor Reaction Time

Sensors were made as described above by depositing 100 uL of a protein A solution (1.0 mg/mL, BioVision, Catalog No. 6500B) on the surface of a piezoelectric base and allowing the solution to dry at 30° C. with circulating air, then depositing 100 uL of anti-Salmonella rabbit polyclonal antibody solution (AbD Serotec, 10 ug/mL or 100 ug/mL, Catalog No. 8209-4006) on the piezoelectric base and allowing the solution to dry at 30° C. with circulating air. A *Salmonella heidelberg* control solution (UC Davis WIFSS, *S. Heidelberg* Strain #10) was diluted to prepare a test solution with a concentration of $10^3$ CFUs/mL.

Each sensor was operatively connected to a system including a lever oscillator circuit and a frequency counter, and a baseline frequency of the sensor was recorded. The sensor was contacted with 100 microliters of test solution or PBS, and the change in frequency was recorded after thirty seconds. Three sensors were tested for each solution, and the data are provided in FIG. 13. The data demonstrate that the SH test solution (concentration of $10^1$ CFUs/mL) could be distinguished from the PBS solution based on delta frequency values at thirty seconds.

Example 6: Analysis of Contribution of Polyclonal Antibody/Protein G Sensor Components to Signal Output Sensors were prepared using different amounts of protein G solution (0.5 mg/mL, BioVision, Inc., Catalog No. 6510) and anti-*Salmonella typhimuriam* (ST) polyclonal goat IgG antibody solution (KPL, Catalog No. 01-91-99). Sensor #1 was prepared with polyclonal antibody only, and no protein G. Sensor #2 was prepared with protein G only, and no polyclonal antibody. Sensor #3 was prepared with both protein G and polyclonal antibody. A *Salmonella typhimuriam* control solution (KPL, Catalog No. 50-74-01) with a concentration of $10^5$ CFUs/mL was used to test the response of each sensor.

Figure 14:
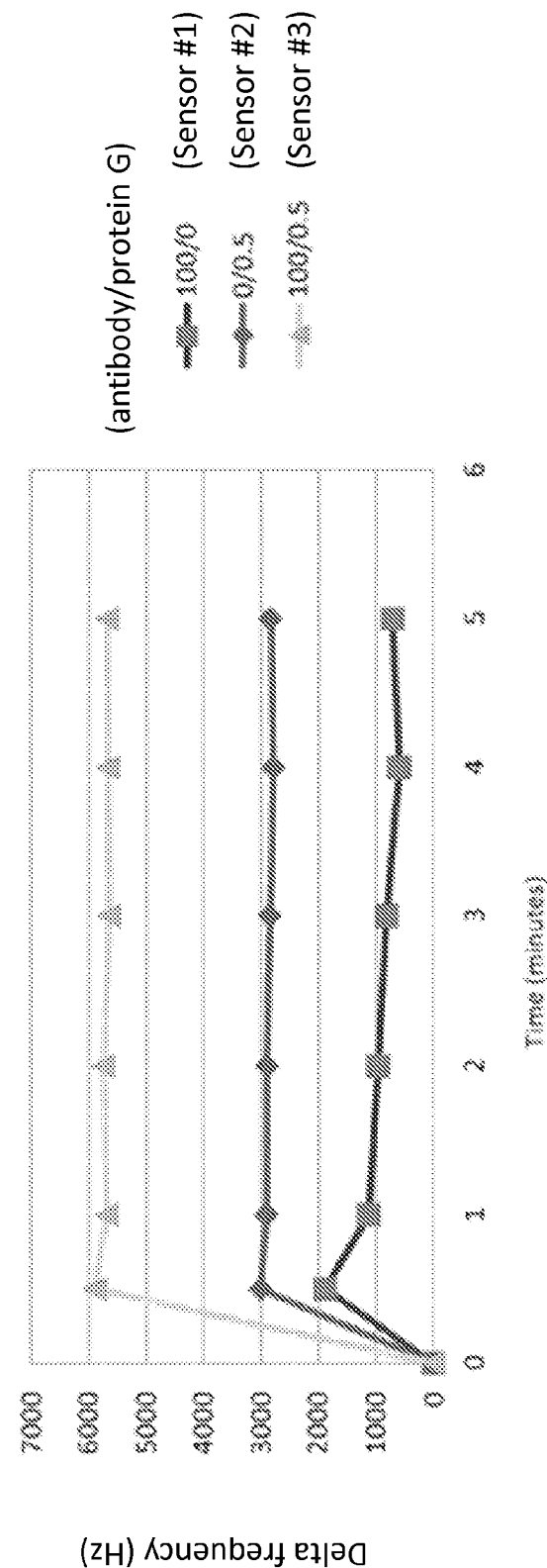
FIG. 14 is a graph showing delta frequency response as a function of time for sensors having three different combinations of components.

Each sensor was operatively connected to a system including a lever oscillator circuit and a frequency counter, and a baseline frequency of the sensor was recorded. The sensor was contacted with 100 microliters of test solution, and the change in frequency over time was recorded. Three sensors were tested at each indicated concentration and time point, and the data are provided in FIG. 14. The data demonstrate that sensor #3, which included both protein G and anti-SH polyclonal antibody, provided the strongest delta frequency response, and that this response reached a plateau value by approximately 30 seconds.

FIG. 15 provides data showing the delta frequency response value at thirty seconds after depositing 100 uL of $10^5$ CFUs/mL test solution on sensors having the indicated amounts of anti-ST polyclonal antibody and protein G or protein A. Three sensors were evaluated for each component combination. The highest delta frequency value (25,828 Hz) was obtained from a sensor that was made from a 100 ug/mL anti-ST polyclonal antibody solution and a 3 mg/mL protein G solution.

As provided in FIG. 15, one sensor type was prepared using protein A (instead of protein G) and the anti-ST polyclonal goat IgG antibody. Protein A does not bind to goat IgG antibodies, and as such, sensors with this combination of components served as a negative control. The data demonstrate that the sensors made with protein A did not provide a strong a delta frequency signal when contacted with the test solution, as was expected.

Example 7: Sensor Utilizing Biotin/Streptavidin Components

Figure 16:
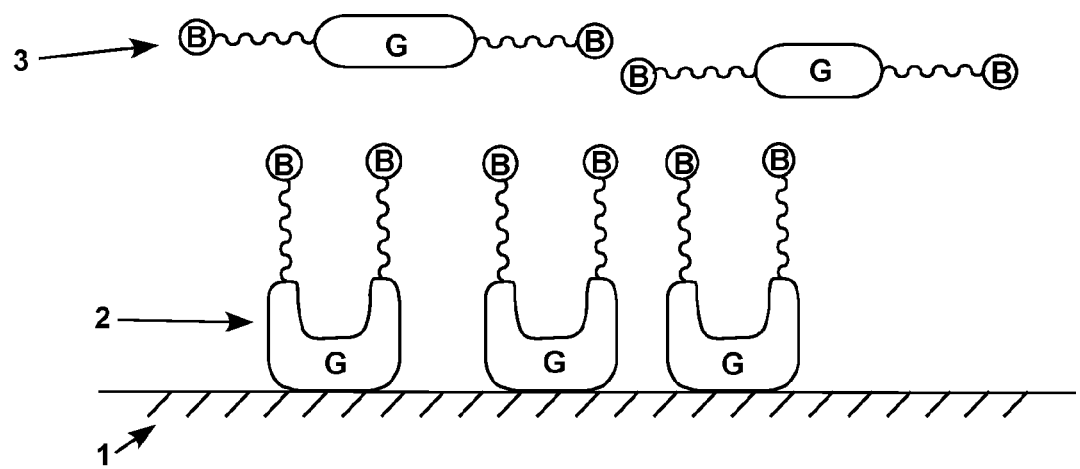
FIG. 16 is a diagram showing a schematic representation of a sensor made with biotin-protein G surface compositions and crosslinking components.

Sensors were prepared using a biotin-protein G solution (100 ug/mL or 10 ug/mL, BioVision, Inc., Catalog No. 6512) whose protein G molecules are biotinylated with approximately 2 biotin molecules per protein G molecule. 100 uL of the biotin-protein G solution was deposited on the surface of a piezoelectric base and allowed to dry at 30° C. with circulating air to form the surface-associated compositions. Next, 100 uL of the same biotin-protein G solution was deposited on top of the surface-associated compositions and allowed to dry at 30° C. with circulating air to form the crosslinking compositions. A schematic illustration of biotin-protein G sensor is provided in FIG. 16. In the depicted embodiment, the piezoelectric base 1 is shown, as well as a plurality of surface-associated compositions 2 and a plurality of crosslinking compositions 3. Each surface-associated composition 2 includes a protein G molecule and two or more biotin molecules. Each crosslinking composition 3 also includes a protein G molecule and two or more biotin molecules. A streptavidin control solution (streptavidin in PBS, Jackson Immunoresearch, Catalog No. 016-000-113) was used as a test solution. Each molecule of streptavidin can bind to four molecules of biotin, thereby crosslinking the surface-associated compositions and the crosslinking compositions.

Each sensor was operatively connected to a system including a lever oscillator circuit and a frequency counter, and a baseline frequency of the sensor was recorded. 100 uL of a 1 mg/mL or 0.1 mg/mL streptavidin test solution, or a phosphate buffered saline (PBS) control solution, were applied to each sensor, and the delta frequency value was measured at 30 seconds. Three sensors were tested with PBS, and four sensors were tested with each streptavidin solution, as indicated in FIGS. 17 and 18. The data demonstrate that the PBS solution could be distinguished from the streptavidin solutions after thirty seconds. Sensors that were made using the 100 ug/mL biotin-protein G solution (as opposed to the 10 ug/mL biotin-protein G solution) showed a greater change in delta frequency when contacted with streptavidin solution v. PBS.

Example 8: Polyclonal Antibody/Protein G Sensor Delta Frequency Response in Liquid State and Dry State Liquid state sensors, in which the components on the surface of the sensor are hydrated, rather than dried, were prepared by depositing 100 uL of a 1 mg/mL protein G solution (BioVision, Inc., Milpitas, Calif., Catalog No. 6512) onto the surface of a piezoelectric base and incubating for 22° C. for 30 minutes. Next, 100 uL of a 100 ug/mL anti-*Salmonella typhimuriam* (ST) polyclonal antibody solution (KPL Laboratories, Catalog No. 01-91-99) was deposited on the surface of the piezoelectric base, and the sensor was again incubated at 22° C. for 30 minutes. The delta frequency of the liquid state sensor was measured and recorded.

Dry sensors were prepared as described above by applying the protein G solution on the surface of a piezoelectric base and allowing the solution to dry at 30° C. with circulating air, then depositing 100 uL of anti-*Salmonella heidelberg* (SH) polyclonal antibody solution on the piezoelectric base and allowing the solution to dry at 30° C. with circulating air.

Each sensor was operatively connected to a system including a lever oscillator circuit and a frequency counter, and a baseline frequency of the sensor was recorded. 100 uL of a *Salmonella typhimuriam* (ST) control solution (KPL, Catalog No. 50-74-01) with a concentration of $10^5$ CFUs/mL, or 100 uL of phosphate buffered saline (PBS), was used to test the response of each sensor. To correct for any mass effects experienced by the liquid state sensor, 300 uL of the ST control solution, or 300 uL of PBS, was also used to test the sensor response. Three sensors were tested for each solution (n=3). The data are provided in FIG. 19. The data indicate that the dry sensors provide a larger delta frequency value as compared to the liquid state sensors.

Example 9: Determination of Limit of Detection (LOD) of *Salmonella* Via ELISA

The limit of detection (LOD) was measured for two different *Salmonella serovars* using a standard ELISA (enzyme linked immune-sorbent assay). The first was *Salmonella Enteritidis* (SE) and the second was *Salmonella heidelberg* (SH). The ELISA was conducted using conjugated biotinylated antibodies with horse radish peroxidase (HRP).

Field strains of SE and SH were grown independently in Tryptic Soy Broth (TSB; Difco, BD) at 37° C. with orbital rotation at 50 rpm for 5 h followed by a refrigeration step at 6° C. for 2 h to stabilize the bacterial growth. Bacterial cells were removed from the growth media (washed) with centrifugation at 10,000 rpm for 10 min; the supernatant (TSB) was discarded and the cells were re-suspended in Phosphate Buffered Saline (PBS; Sigma-Aldrich, St. Louis, Mo.). Cell counts were estimated using a regression equation that extrapolated bacterial concentration from the optical density at 600 nm; 1 mL of the washed cell-suspension was 10-fold serial diluted in PBS to obtain the target concentrations of $10^6$-$10^2$ CFU/mL. Cell counts were confirmed by spread plating the serial dilutions onto tryptic soy agar (TSA; Difco, BD) and incubating at 37° C. for 18 to 24 h.

Both capture antibodies (SH was a polyclonal and SE was a monoclonal) were diluted in 0.2 M sodium carbonate/bicarbonate, pH 9.4. Then 100 uL of capture antibody were added to each well. The plate was covered and incubated at 4° C. The next day, the solution was removed and washed with 200 uL of PBS in each well, three times for 5 minutes each on a shaking platform. After washing, 300 uL of blocking buffer (2% BSA in PBS) were added to each well and incubated overnight at 4° C. The next day, the blocker was removed and 100 uL of antigen were added to each well. The plate was then incubated at room temperature for 1 hour. The samples were removed and the plate was washed with PBS. Afterwards, 100 uL of the biotinylated detection antibody was added to each well and the plate was incubated at room temperature for another hour. Then the solution was removed and the plate was washed with PBS three times. Next, streptavidin-HRP served as the enzyme conjugate and 100 uL were added to each well. The plate was then covered and incubated at room temperature for 1 hour. The solution was removed and the plate was washed 6 times with PBS. TMB served as the substrate solution and 100 uL were added to each well and the plate was incubated at room temperature. After 15 minutes, the absorbance at 650 nm was taken using a spectrometer.

The results established that the LOD for SE was $10^4$, and the LOD for SH was $10^6$ CFUs/mL when measured via ELISA. The SE and SH capture antibodies cross reacted against the SH and SE antigens at $10^7$ CFUs/mL. However, the $OD_{650}$ values were lower for the cross-reacted antigen than for the target antigen. The results are provided in FIG. 20. The top number in each cell is the $OD_{650}$ value without subtracting the blank value, and the bottom number is the $OD_{650}$ value with the blank value subtracted.

Example 10: Use of Activated Carbon to Increase Detection

Sensors were made as described above by applying the protein G solution on the surface of a piezoelectric base and allowing the solution to dry at 30° C. with circulating air, then depositing 100 uL of anti-*Salmonella typhimuriam* antibody solution (10 ug/mL, KPL Labs, Catalog No. 01-91-99) on the piezoelectric base and allowing the solution to dry at 30° C. with circulating air. In certain sensors, approximately 1 ug of activated, micronized carbon (Cabot Corp.) was applied to and evenly dispersed over the piezoelectric base during production. A *Salmonella typhimuriam* positive control (ST pos. control) with a concentration of $10^5$ CFUs/mL (KPL Labs, Catalog No. 50-74-01), phosphate buffered saline (PBS) solution, or activated carbon solution was used to test the response of the sensors.

Each sensor was operatively connected to a system including a lever oscillator circuit and a frequency counter, and a baseline frequency of the sensor was recorded. The sensor was contacted with 100 microliters of test solution (either ST pos. control, PBS, or activated carbon solution), and the change in frequency over time was recorded. The data are provided in FIG. 21. The results show that the inclusion of activated carbon in the sensor increases the mean delta frequency of response by approximately 5×.

Figure 22:
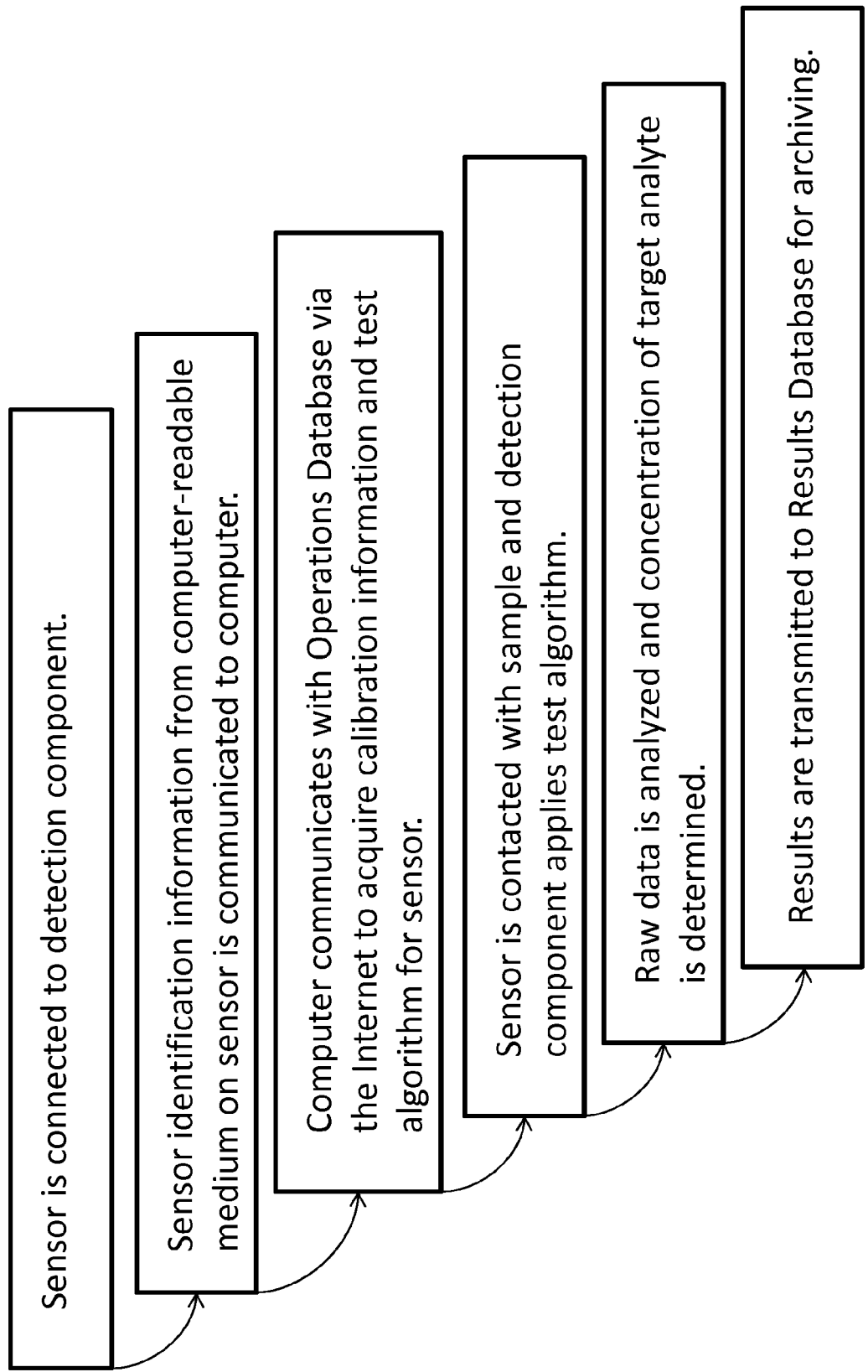
FIG. 22 is a flow diagram that shows the steps of a method for determining a concentration of a target analyte in an unknown sample using an Internet-enabled system.

Example 11: Method for Determining Analyte Concentration in an Unknown Sample Using an Internet-Enabled System FIG. 22 is flow diagram illustrating the steps involved with using an Internet-enabled system to determine the concentration of a target analyte in an unknown sample. First, a sensor is connected to a detection component. Sensor identification information stored on a computer readable medium on the sensor is read by the detection component and communicated to the computer. The computer then communicates with an operations database via the Internet to acquire calibration information and test algorithm information for the particular sensor. Next, the sensor is contacted with a sample containing an unknown concentration of a target analyte. The detection component applies the test algorithm and the raw data is analyzed. The computer applies the calibration information to the raw data to determine the concentration of the target analyte in the sample. The results are communicated to a user via a GUI on the detection component. The results are also transmitted to a results database via the Internet, where the results are archived.

Figure 23:
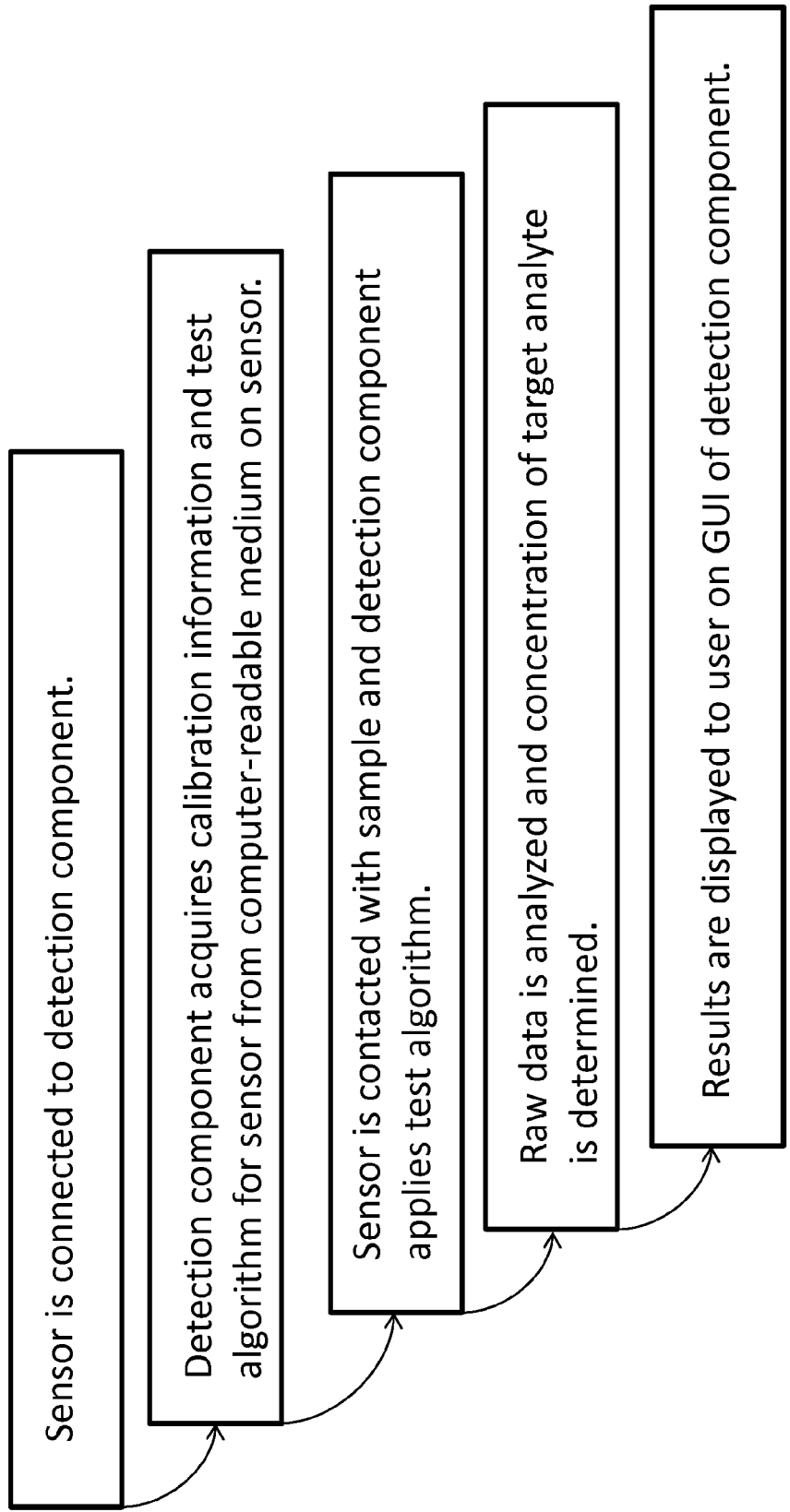
FIG. 23 is a flow diagram that shows the steps of a method for determining a concentration of a target analyte in an unknown sample using a non-Internet-enabled system.

Example 12: Method for Determining Analyte Concentration in an Unknown Sample Using a Non-Internet-Enabled System FIG. 23 is flow diagram illustrating the steps involved with using a non-Internet-enabled system to determine the concentration of a target analyte in an unknown sample. First, a sensor is connected to a detection component. Sensor identification information stored on a computer readable medium on the sensor is read by the detection component. The sensor identification information includes calibration information as well as test algorithm information that is used by the detection component when analyzing a sample. Next, the sensor is contacted with a sample containing an unknown concentration of a target analyte. The detection component applies the test algorithm and the raw data is analyzed. The detection component applies the calibration information to the raw data to determine the concentration of the target analyte in the sample. The results are communicated to a user via a GUI on the detection component.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of making a sensor, the method comprising:
   depositing a plurality of surface-associated compositions on a piezoelectric base, wherein the plurality of surface-associated compositions are adapted to stably associate with the piezoelectric base; and
   depositing a plurality of crosslinking compositions on top of the surface-associated compositions, wherein the crosslinking compositions are configured to bind to an analyte and crosslink one or more of the surface-associated compositions when the analyte binds to an analyte binding domain of a crosslinking composition.

2. The method according to claim 1, wherein the surface-associated compositions comprise one or more of: protein A, protein G, protein A/G, or protein L.

3. The method according to claim 1, wherein the crosslinking compositions comprise one or more of: protein A, protein G, protein A/G, or protein L.

* * * * *